US007803842B2

(12) United States Patent
Patel

(10) Patent No.: US 7,803,842 B2
(45) Date of Patent: Sep. 28, 2010

(54) CHOLINE ESTERS USEFUL FOR THE TREATMENT OF COGNITIVE DYSFUNCTIONS AND ENHANCEMENT OF MEMORY, LEARNING AND COGNITION

(75) Inventor: Hasmukh B. Patel, Edison, NJ (US)

(73) Assignee: Hass Patel, Edison, NJ (US)

(*) Notice: Subject to any disclaimer, the term of this patent is extended or adjusted under 35 U.S.C. 154(b) by 136 days.

(21) Appl. No.: 11/354,576

(22) Filed: Feb. 15, 2006

(65) Prior Publication Data

US 2006/0205815 A1 Sep. 14, 2006

Related U.S. Application Data

(63) Continuation of application No. PCT/US2004/023400, filed on Jul. 20, 2004.

(60) Provisional application No. 60/578,503, filed on Jun. 8, 2004.

(51) Int. Cl.
 *A61K 31/00* (2006.01)
(52) U.S. Cl. .................................................. 514/642
(58) Field of Classification Search .................. 514/642
 See application file for complete search history.

(56) References Cited

U.S. PATENT DOCUMENTS

| 4,260,529 A | 4/1981 | Letton |
| 4,713,376 A | 12/1987 | Kuzuya et al. |
| 4,963,556 A | 10/1990 | Alexander et al. |

| 6,153,653 A | * | 11/2000 | Shashoua .................... 514/642 |

FOREIGN PATENT DOCUMENTS

| WO | WO 0181296 | * 11/2001 |
| WO | WO-0181296 A1 | 11/2001 |

OTHER PUBLICATIONS

Oda, Y., Choline acetyltransferase: The structure, distributio and pathologic changes in the central nervous system, 1999, Pathology International, vol. 49, pp. 921-937.*
Reedler, T. J. et al., In Vivo determination of muscarinic acetylcholine receptor availability in schizophrenia, 2003, Am. J. Psychiatry, vol. 160, pp. 118-127.*
Meyerhoff, D.J. et al., Elevated subcortical choline metabolites in cognitively and clinically asymptomatic HIV+ patients, 1999, Neurology, vol. 52(5), pp. 1-15.*
Odawa, T. et al., Alterations of muscarinic acetylcholine receptors in atypical pick's disease without Pick bodies, 2003, j. neurol Neurosurg Psychiatry, vol. 74, pp. 965-967.*

(Continued)

*Primary Examiner*—Daniel M Sullivan
*Assistant Examiner*—Yate' K Cutliff
(74) *Attorney, Agent, or Firm*—Schwegman, Lundberg & Woessner, P.A.

(57) ABSTRACT

The present invention provides compounds of formula I described herein. The present invention also provides a method of treating a cognitive dysfunction in a mammal. The method includes administering to the mammal an effective amount of a compound of formula I described herein (e.g., stearyl choline chloride).

13 Claims, 4 Drawing Sheets

OTHER PUBLICATIONS

Amaral, L. et al., phenothiazines; Potential management of Creutzfeldt-Jacob disease and its variants, 2001, International Journal of Antimicrobial Agents, vol. 18, pp. 411-417.*

Parnetti, L., Choline Alphoscerate in cognitive decline and in acute cerebrovascular disease: an analysis of publshed clincal data, 2001, Mechanisms of Ageing and Deveeloopment, vol. 122, pp. 2041-2055.*

Mayeux, R. et al., Treatment of Alzheimer's Disease, 1999, The New England Journal of Medicine, vol. 341, No. 22, pp. 1670-1679 (10 pages).*

Clausen, S., et al., "Separation of Aromatic Choline Esters by High-Performance Liquid Chromatography", *Journal of Chromatography, 260*, (1983),193-199.

Szulc, Z., et al., "Synthesis of Choline Ester of 9-Oxo-10-Acridineacetic Acid and of Congeners as Potential Interferon Inducers", *Polish Journal of Chemistry, 60*, (1986),615-619.

"International Application No. PCT/US2004/023400 Demand and Article 34 Amendment filed May 4, 2005", 17 pgs.

"International Application No. PCT/US2004/023400 International Preliminary Report on Patentability mailed Jun. 12, 2005", 12 pgs.

"International Application No. PCT/US2004/023400 International Search Report and Written Opinion mailed Jan. 28, 2005", 13 pgs.

Adams, Harold P., et al., "Guidelines for the Early Management of Adults With Ischemic Stroke", *Stroke 38*, accessed on-line at "http://stroke.ahajournals.org/cgi/reprint/STROKEAHA.107.181486" on Sep. 17, 2008, (Apr. 12, 2007), 1655-1711.

Adams, Robert J., et al., "Update to the AHA/ASA Recommendations for the Prevention of Stroke in Patients With Stroke and Transient Ischemic Attack" *Stroke 39*, on-line reprint accessed at "http://stroke.ahajournals.org/cgi/reprint/STROKEAHA.107.189063" on Sep. 17, 2008, (May 2008), 1647-1652.

Caselli, R. J, "Current issues in the diagnosis and management of dementia.", *Semin. Neurol., 23(3)*, (Sep. 2003), 231-40.

Chui, H., "Vascular dementia, a new beginning: shifting focus from clinical phenotype to ischemic brain injury.", *Neurol Clin., 18(4)*, (Nov. 2000), 951-78.

Shadlen, Marie-Florence, et al., "Dementia syndromes", *UpToDate Database*, (2008).

Wright, Clinton B, "Etiology, clinical manifestations, and diagnosis of vascular dementia", *UpToDate Database*, (2008).

Higgins, J. P, et al., "Lecithin for dementia and cognitive impairment.", *Cochrane Database Syst Rev. (4)*, (2000), CD001015.

Stewart, R. M, et al., "Receptor mechanisms in increased sensitivity to serotonin agonists after dihydroxytryptamine shown by electronic monitoring of muscle twitches in the rat.", *Psychopharmacology (Berl)., 60(3)*, (Feb. 28, 1979), 281-9.

* cited by examiner

Water Maze Hidden Platform Test

CHOLINE ESTERS USEFUL FOR THE TREATMENT OF COGNITIVE DYSFUNCTIONS AND ENHANCEMENT OF MEMORY, LEARNING AND COGNITION

CLAIM OF PRIORITY

This patent application is a continuation under 35 U.S.C. 111(a) of PCT US2004/023400 filed on Jul. 20, 2004, and published in English on Mar. 3, 2005 as WO2005/019157 A1, which claims the benefit of priority to U.S. patent application Ser. No. 10/642,455, filed Aug. 15, 2003, to International Patent Application No. PCT/US03/27062, filed Aug. 29, 2003 and to U.S. Provisional Patent Application Ser. No. 60/578,503, filed Jun. 8, 2004, which applications are herein incorporated by reference.

BACKGROUND OF THE INVENTION

Alzheimer's disease (AD) is a progressive, degenerative disease of the brain. Alzheimer's disease is one of several disorders that cause the gradual loss of brain cells. German physician Dr. Alois Alzheimer first described the disease in 1906. Although the disease was once considered rare, research has shown that it is the leading cause of dementia.

Dementia is an umbrella term for several symptoms related to a decline in thinking skills. Common symptoms include a gradual loss of memory, problems with reasoning or judgment, disorientation, difficulty in learning, loss of language skills, and decline in the ability to perform routine tasks. People with dementia also experience changes in their personalities and behavioral problems, such as agitation, anxiety, delusions (believing in a reality that does not exist), and hallucinations (seeing things that do not exist).

Several disorders that are similar to Alzheimer's disease can cause dementia. These include fronto-temporal dementia, dementia with Lewy bodies, Parkinson's disease, Creutzfeldt-Jakob disease, and Huntington's disease. All of these disorders involve disease processes that destroy brain cells.

Vascular dementia is a disorder caused by the disruption of blood flow to the brain. This may be the result of a massive stroke or several tiny strokes. Some treatable conditions—such as depression, drug interactions, and thyroid problems—can cause dementia. If treated early enough, this dementia may be effectively treated and even reversed.

According to the Alzheimer's Association website, Oct. 31, 2002 (http://www.alz.org):

Approximately 4 million Americans have AD. In a 1993 national survey, 19 million Americans said they had a family member with AD, and 37 million said they knew someone with AD;

14 million Americans will have AD by the middle of this century (2050) unless a cure or prevention is found;

One in 10 persons over 65 and nearly half of those over 85 have AD;

A small percentage of people as young as their 30's and 40's get the disease;

A person with AD will live an average of eight years and as many as 20 years or more from the onset of symptoms;

U.S. society spends at least $100 billion a year on treatment and care of persons with AD;

Neither Medicare nor most private health insurance covers the long-term care most patients need. Alzheimer's disease is costing American business $61 billion a year—$36.5 billion is the cost to business of caregiving (lost productivity from absenteeism of employees who care for family members with Alzheimer's); the rest is the business share of the costs of health and long-term care;

More than 7 of 10 people with Alzheimer's disease live at home. Almost 75% of the home care is provided by family and friends. The remainder is "paid" care costing an average of $12,500 per year. Families pay almost all of that out-of-pocket;

Half of all nursing home residents suffer from AD or a related disorder. The average cost for nursing home care is $42,000 per year but can exceed $70,000 per year in some areas of the country. The average lifetime cost per patient is $174,000; and The Alzheimer's Association has granted nearly $120 million dollars in research grants (since 1982). The federal government estimates spending approximately $598.9 million for Alzheimer disease research in FY2002.

Alzheimer's disease advances at widely different rates. The duration of the illness can vary from 3 to 20 years. The areas of the brain that control memory and thinking skills are affected first, but as the disease progresses, cells die in other regions of the brain. Eventually, the person with Alzheimer's will need complete care. If the individual has no other serious illness, the loss of brain function itself will cause death.

No one knows yet exactly what causes Alzheimer's disease. Researchers are learning about what happens to the brain as we grow older, what happens to brain cells in Alzheimer's disease, genes associated with Alzheimer's, and many other factors that may be important. Most researchers agree that the cause may be a complex set of factors.

Studies have shown that the greatest known risk for developing Alzheimer's is increasing age. As many as 10 percent of all people 65 years of age and older have Alzheimer's. As many as 50 percent of all people 85 and older have the disease. A family history of the disease is another known risk. Having a parent or sibling with the disease increases an individual's chances of developing Alzheimer's.

There is no cure for Alzheimer's disease. However, there are several drug treatments that may improve or stabilize symptoms and several care strategies and activities that may minimize or prevent behavioral problems. Researchers continue to look for new treatments to alter the course of the disease and other strategies to improve the quality of life for people with dementia.

Mild cognitive impairment (MCI), operationally defined as isolated episodic memory decline, has recently emerged as the clinical entity that most conveniently and reliably represents incipient Alzheimer's disease (AD). *Arch. Neurol.*, 58:1985 (2001). The risk of conversion to AD is higher in MCI than in the general aged population, as up to 50% of these patients develop the disease within two years. *Neurology*, 41:1006 (1991). Additionally, MCI is associated with an increased risk of developing dementia: patients develop dementia at a rate of 10-15% per year compared with healthy controls who develop dementia at a rate of 1-2% per year. *Acta. Psychiatr. Scand.*, 106:403 (2002).

Glutamate is one neurotransmitter implicated in Alzheimer's disease. Glutamate is the principal excitatory amino acid neurotransmitter in cortical and hippocampal neurons. *Neurology*, 46:661-65 (1996). Accumulating evidence suggests that the cortical neuronal loss underlying dementia may be related to an increased sensitivity to glutamate and/or sustained elevations of glutamate levels. *Int. J. Geriatr. Psychiatry*, 14:3 (1999). This leads to a cumulative influx of calcium into neurons, impaired neuronal homeostasis, and eventually neurodegeneration, resulting in cell death. *Biol. Psychiatry*, 41:135 (1997); *Prog. Brain. Res.*, 116:331

(1998); and *Neurobiol. Aging,* 10:593 (1989). One of the receptors activated by glutamate is the N-methyl-D-aspartate (NMDA) receptor, which is involved physiologically in learning and memory. *Pharmacol. Review,* 50:597 (1998). Because excessive NMDA receptor stimulation induced by ischemia leads to excitotoxicity (*Prog. Brain Res.,* 116:331 (1998)), agents that block pathological stimulation of NMDA receptors might be anticipated to protect against further cortical neurodegeneration in dementia while the physiological function of the remaining neurons could be restored, resulting in symptomatic improvement. *J. Neural. Trans. Suppl.,* 43:91 (1994).

Noradrenaline, also known as norepinephrine (NE) is another key neurotransmitter that may be involved in Alzheimer's disease. Disruption of normal noradrenergic (NA) functions has been implicated in the pathophysiology of both schizophrenia and AD. *Biol. Psychiatry,* 46:1243 (1999).

The locus ceruleus (LC) is the main subcortical site of norepinephrine (NE) synthesis and its precursor enzymes. Noradrenergic axons arising from the LC neurons project to several cortical areas, including the hippocampus, entorhinal cortex, and frontal cortex, where their axon terminals are in close contact with neurons, astrocytes, and brain microvessels. *Neurosci. Lett.,* 97:203 (1989) and *Brain Res. Bull.,* 45:247 (1998). The LC-generated NE plays an important role in selective attention, general arousal, and stress reactions in response to challenging environmental situations. *Physiol. Rev.,* 63:844 (1983) and *Brain Res.,* 531:189 (1990).

Two distinct cellular projections are involved in the central noradrenergic system: those originating from the ventrolateral tegmental noradrenergic cells, which are associated mainly with sexual and feeding behaviors; and those originating from the locus ceruleus (LC) cells, which are associated with certain cognitive functions (Crow, *Nature,* 219:736 (1968); Mason and Iversen, *Brain Res. Rev.,* 1:107 (1979)). Furthermore, the prefrontal cortex (PFC) is rich in noradrenergic terminal fields from the LC, where it is believed that norepinephrine (NE) acts to reduce distractibility by strengthening PFC function. It is also believed that the PFC contributes to the cognitive dysfunction seen in a variety of neuropsychiatric disorders (e.g., attention deficit hyperactivity disorder (ADHD), Korsakoff's syndrome, and schizophrenia; Arnsten et al., *Arch. Gen. Psychiatry,* 53:448 (1996)). Therefore, dysfunction of noradrenergic receptors in the PFC could contribute to the pathophysiology of cognitive dysfunction associated with these conditions.

Cognitive deficits, similar to those seen in the neuropsychiatric disorders just mentioned, can be produced in animals by producing lesions of the LC noradrenergic system. These include deficits in sustained attention (Carli et al., *Behav. Brain Res.,* 9:361 (1983); Cole and Robbins, *Neuropsychopharmacology,* 7:129 (1992)) and shifting attention (Devauges and Sara, *Behav. Brain Research,* 39:19 (1990)). In addition, rats with lesions of the LC demonstrate impaired learning directly associated with decreased levels of cortical NE (Anlezark et al., *Science,* 181:682 (1973)). These deficits are reversible with the administration of drugs that enhance noradrenergic neurotransmission. For example, the administration of diethyldithiocarbamate (DDC), an inhibitor of the enzyme dopamine-beta-hydroxylase (DBH), to rats depletes NE stores in the brain, and produces complete retention failure of passive avoidance learning (Hamburg and Cohen, *Pharmacol. Biochem. Behav.,* 1:295 (1973); Stein et al., *Brain Res.,* 84:329(1975)). Subsequently, normal learning of the passive avoidance task is restored in DDC-treated rats with a single intraventricular dose of NE (Stein et al., *Brain Res.,* 84:329 (1975)). In addition, puromycin-induced amnesia for maze learning in rats is reversed by the administration of drugs increasing noradrenergic activity, such as imipramine, tranylcypromine, and D-amphetamine (Roberts et al., *Proc. Natl. Acad. Sci. USA,* 66:310 (1970)).

However, drugs that nonspecifically increase noradrenergic activity, such as tricyclic antidepressants, monoamine oxidase inhibitors, amphetamines, and specific norepinephrine reuptake inhibitors, may be detrimental to cognition in neuropsychiatric conditions where PFC functions are compromised.

Experimentally induced loss of LC neurons (which, again, are involved in the noradrenergic system) has been implicated in learning and behavior deficits. *Science,* 181:682 (1973); *Nature,* 285:422 (1975); and *J. Neurol. Transcm.,* 106:619 (1999). Loss of LC neurons, degeneration of noradrenergic (NA) projections, and a decrease in cortical NE levels are well-described features of various neurodegenerative diseases, including AD and Parkinson's disease. *Journal of Neuroscience,* 22(7):2434 (2002). In addition, decreased LC neuronal counts are significantly correlated with the severity of dementia in AD.

Thus, two classic pathological hallmarks of AD are LC loss and decreased noradrenergic (NA) innervation. Recent evidence suggests a link between these two. *Neurobiol. Aging,* 21:383 (2000). It has been hypothesized that neuronal LC loss and neuropathological and inflammatory changes are members of a vicious self-maintaining and self-stimulating cycle, with no guidance at which point and by what treatment a beneficial interruption of this cycle can be achieved. *Neurobiol. Aging,* 21:383 (2000).

Another neurotransmitter that may be involved in Alzheimer's disease is serotonin. Over the last decades, extensive evidence has suggested that serotonin and the serotonergic system plays an important modulatory role in learning and memory through action on specific receptors and interaction with multiple neurotransmitter systems, such as glutamatergic, cholinergic, dopaminergic or GABAergic pathways. *Annals of Medicine,* 32:210 (2000). Because of their distribution in the limbic areas and in the frontal cortex (*Neuropharmacology,* 33:527 (1994)), serotonin receptors are proposed to be involved in cognitive processes. *British Journal of Pharmacology* 115, 1387-1392 (1995) and *Neuropharmacology,* 38:1083 (1999). Neurochemical, electrophysiological and behavioral studies support a role for those receptors in cholinergically-mediated memory process.

Serotoninergic and cholinergic manipulations are known to influence cognition. *Neuroscience,* 69:1 (1995) and *European Journal of Neuroscience,* 12:67 (2000). Post-mortem studies revealed that the hippocampal serotonin receptor density declines in patients with cholinergic and memory alterations such as those observed in AD. *Behavior and Brain Research* 73:249 (1996). Overall, results of the literature suggest that serotonin receptor agonists may improve the rate of learning; however, most of the available arguments have been obtained under pre-induced, altered, conditions and almost no information is available in normal conditions. *Neuropharmacology.* 41:517 (2001).

Patients with Alzheimer dementia frequently have severe reductions in brain cholinergic and serotonergic function (*Semin. Neurosci.* 2:101 (1990)), suggesting that simultaneous reduction of cholinergic and serotonergic function in animals might provide a model of global dementia and amnesia. *Brain Research* 111: 125 (2000).

Thus, evidence suggests that the dementing and amnesic effects of Alzheimer's disease may result from alterations or damage to a number of different neurotransmitter systems and neuronal pathways. *Neurobiol. Aging* 14:343 (1993);

Trends Neurosci. 14:220 (1991); Neurotransmitters and neuropeptides In: Alzheimer's Disease, Katzman (ed.) 247-61 (1994). Neurobiol. Aging 10:593 (1987); and J. Neurosci. 14:6317 (1994). However, there exists a lack of complete understanding of the varied neurotransmitter system and behavioral impairments found in human Alzheimer patients. Semin. Neurosci., 2:101 (1990); Annal. Neurol. 29:41 (1991); Trends Neurosci. 14:220 (1991). Additionally, the use of atypical antipsychotics to address the cognitive impairments of dementia (e.g., AD) has met with only limited success. Society of Biol. Psychiatry, 46:1243 (1999). Clearly, one problem with these strategies is that they ignore the influence of a multiplicity of lesions on the manifestation of these illnesses.

U.S. Pat. No. 4,624,852 is directed toward compositions useful for treating neurological disorders and aging. The compositions include: (a) choline or a choline precursor and (b) an amino acid which is a precursor to a neurotransmitter. The choline or choline precursor and amino acid are administered to a patient concomitantly. See, col. 2, lines 14-28. The choline or choline precursor and amino acid are co-administered to provide a synergistic result for the two components. See, Abstract. The choline can be administered as choline salts or esters. See, col. 2, lines 46-47. The specific esters disclosed therein include chloride bitartrate or stearate or the like, or as a compound that dissociates to choline, such as sphingomyelin, cytidine-diphospho-choline, an acylglycerophosphocholine, e.g., lecithin, lysolecithin, glycerophosphatidyl choline, mixtures thereof or the like. See, col. 2, lines 46-54.

Rispoli, et al., Neuroscience Letters, 356:199 (2004) is directed toward the use of choline pivaloyl esters to improve cognitive and memory performances. The two choline pivaloyl esters disclosed therein are: [2-(2,2-dimethylpropionyloxy)ethyl]trimethylammonium iodine and [2-(2,2-dimethylpropionyloxy)ethyl]trimetrhylammonium 2,2-dimethylpropionate. See, Abstract.

U.S. Pat. No. 4,963,556 is directed toward choline esters useful for drug absorption enhancing agents for drugs which are poorly absorbed from the nasal, oral, and vaginal cavities. See, Abstract. The choline esters are compounds of the formula:

wherein R is saturated acyl ($C_2$-$C_{20}$), acyl ($C_2$-$C_{20}$) with 1 to 6 double bonds, hydroxyacyl ($C_2$-$C_{20}$) with 1 to 3 hydroxy groups, ketoacyl ($C_4$-$C_{20}$), unsaturated hydroxyacyl ($C_5$-$C_{20}$), alkylaryl ($C_7$-$C_{20}$) arylacyl ($C_7$-$C_{20}$), alkylaryl ($C_7$-$C_{20}$) or carbalkoxyacyl ($C_5$-$C_{20}$) and X is a pharmaceutically acceptable counterion. See, claim 1. There is no disclosure or suggestion in the '556 patent that the choline esters described therein will have any therapeutic activity (e.g., useful in treating Alzheimer's disease).

U.S. Pat. No. 4,647,580 is directed toward tertiary amines useful for treating senile dementia of the Alzheimer's type. The tertiary amines are shown below:

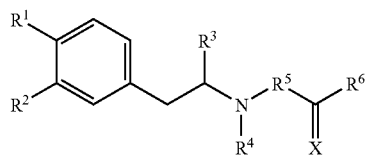

wherein, $R^1$ is alkyl, alkoxy, alkylthio or dialkylamino hydroxyl, hydrogen, chlorine or fluorine; $R^2$ is hydrogen, or when $R^1$ is hydrogen, alkyl, alkoxy, alkylthio, alkylthioamino, hydroxyl, chlorine or fluorine; $R^3$ is 1 to 2 carbon alkyl; $R^4$ is 1 to 3 carbon alkyl; $R^5$ is an optionally branched 3 to 12 carbon alkylene; X is oxygen or ethylene dioxy; and $R^6$ is optionally branched or cyclic carbon group having less than eight carbons. See, Abstract.

New therapeutic strategies must be designed to accommodate the diverse neurochemical deficits seen in the AD population by restoring the functional integrity of a number of affected systems.

SUMMARY OF THE INVENTION

The present invention provides a compound of formula (I):

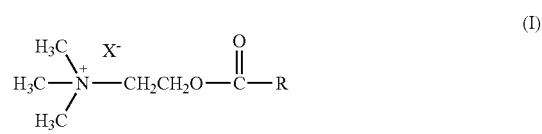

wherein,

R is straight-chain or branched chain, saturated or unsaturated alkyl, alkoxy, haloalkyl, hydroxyalkyl, aryl, heteroaryl, heterocycle, cycloalkyl, alkylamino, trifluoromethyl, trifluoromethoxy, alkylthio, alkylsulfinyl, or alkylsulfonyl; and X is a pharmaceutically acceptable counterion; or a pharmaceutically acceptable salt thereof.

The present invention also provides a pharmaceutical composition that includes a pharmaceutically acceptable carrier or diluent, and a compound of formula (I).

The present invention also provides a method of treating a cognitive dysfunction in a mammal, the method includes administering to the mammal an effective amount of a choline ester.

The present invention also provides a method of treating a cognitive dysfunction in a mammal, the method includes administering to the mammal an effective amount of a compound of formula (I).

The present invention also provides a method of improving cognition functions in a mammal suffering from Alzheimer's disease type dementia, the method includes administering to the mammal an effective amount of a choline ester.

The present invention also provides a method of improving cognition functions in a mammal suffering from Alzheimer's disease type dementia, the method includes administering to the mammal an effective amount of a compound of formula (I).

The present invention also provides a method of treating down syndrome in a mammal suffering from down syndrome, the method includes administering to the mammal an effective amount of a choline ester.

The present invention also provides a method of treating down syndrome in a mammal suffering from down syndrome, the method includes administering to the mammal an effective amount of a compound of formula (I).

The present invention also provides a method of treating central nervous system (CNS) disorders in a mammal suffering from central nervous system (CNS) disorders, the method includes administering to the mammal an effective amount of a compound of a choline ester.

The present invention also provides a method of treating central nervous system (CNS) disorders in a mammal suffering from central nervous system (CNS) disorders, the method includes administering to the mammal an effective amount of a compound of a compound of formula (I).

The present invention also provides a method of treating peripheral nervous system (PNS) disorders in a mammal suffering from peripheral nervous system (PNS) disorders, the method includes administering to the mammal an effective amount of a compound of a choline ester.

The present invention also provides a method of treating peripheral nervous system (PNS) disorders in a mammal suffering from peripheral nervous system (PNS) disorders, the method includes administering to the mammal an effective amount of a compound of a compound of formula (I).

The present invention also provides a method of treating memory related disorders in a mammal suffering from memory related disorders, the method includes administering to the mammal an effective amount of a compound of a choline ester.

The present invention also provides a method of treating memory related disorders in a mammal suffering from memory related disorders, the method includes administering to the mammal an effective amount of a compound of a compound of formula (I).

The present invention also provides a method of improving learning and behavior in a mammal suffering from diminished learning and behavior levels, the method includes administering to the mammal an effective amount of a compound of a choline ester.

The present invention also provides a method of improving learning and behavior in a mammal suffering from diminished learning and behavior levels, the method includes administering to the mammal an effective amount of a compound of a compound of formula (I).

The present invention also provides a method of improving cognition in a mammal suffering from diminished cognition levels, the method includes administering to the mammal an effective amount of a compound of a choline ester.

The present invention also provides a method of improving cognition in a mammal suffering from diminished cognition levels, the method includes administering to the mammal an effective amount of a compound of a compound of formula (I).

The present invention also provides a method of enhancing PNS functions in a mammal suffering from diminished PNS function levels, the method includes administering to the mammal an effective amount of a compound of a choline ester.

The present invention also provides a method of enhancing PNS functions in a mammal suffering from diminished PNS function levels, the method includes administering to the mammal an effective amount of a compound of a compound of formula (I).

The present invention also provides a method of enhancing CNS functions in a mammal suffering from diminished CNS function levels, the method includes administering to the mammal an effective amount of a compound of a choline ester.

The present invention also provides a method of enhancing CNS functions in a mammal suffering from diminished CNS function levels, the method includes administering to the mammal an effective amount of a compound of a compound of formula (I).

The present invention also provides a method of enhancing memory and related functions in a mammal suffering from diminished memory and related function levels, the method includes administering to the mammal an effective amount of a compound of a choline ester.

The present invention also provides a method of increasing or enhancing memory, learning, cognition, or a combination thereof in a healthy mammal, the method includes administering to the mammal an effective amount of a compound of formula (I).

The present invention also provides a method of increasing or enhancing memory, learning, cognition, or a combination thereof in a healthy mammal, the method includes administering to the mammal an effective amount of a choline ester.

The present invention also provides a method of enhancing memory and related functions in a mammal suffering from diminished memory and related function levels, the method includes administering to the mammal an effective amount of a compound of a compound of formula (I).

The present invention also provides a method of treating Parkinson's Disease in a mammal, the method includes administering to the mammal an effective amount of a compound of a choline ester.

The present invention also provides a method of treating Parkinson's Disease in a mammal, the method includes administering to the mammal an effective amount of a compound of a compound of formula (I).

The present invention also provides a method for the treatment of Acetylcholine related CNS and PNS disorders, or for enhancement or improvement those functions in normal and/or diseased mammals, the method includes administering to the mammal an effective amount of a choline ester.

The present invention also provides a method for the treatment of Acetylcholine related CNS and PNS disorders, or for enhancement or improvement those functions in normal and/or diseased mammals, the method includes administering to the mammal an effective amount of a compound of formula (I).

The compounds of the present invention possess a suitable therapeutic index. The compounds of the present invention also possess a suitable absorption profile, through the gastrointestinal (GI) tract. The compounds of the present invention also possess minimal side-effects. The compounds of the present invention also possess a suitable penetration profile through the blood-brain barrier.

DETAILED DESCRIPTION OF THE INVENTION

Figure 1:
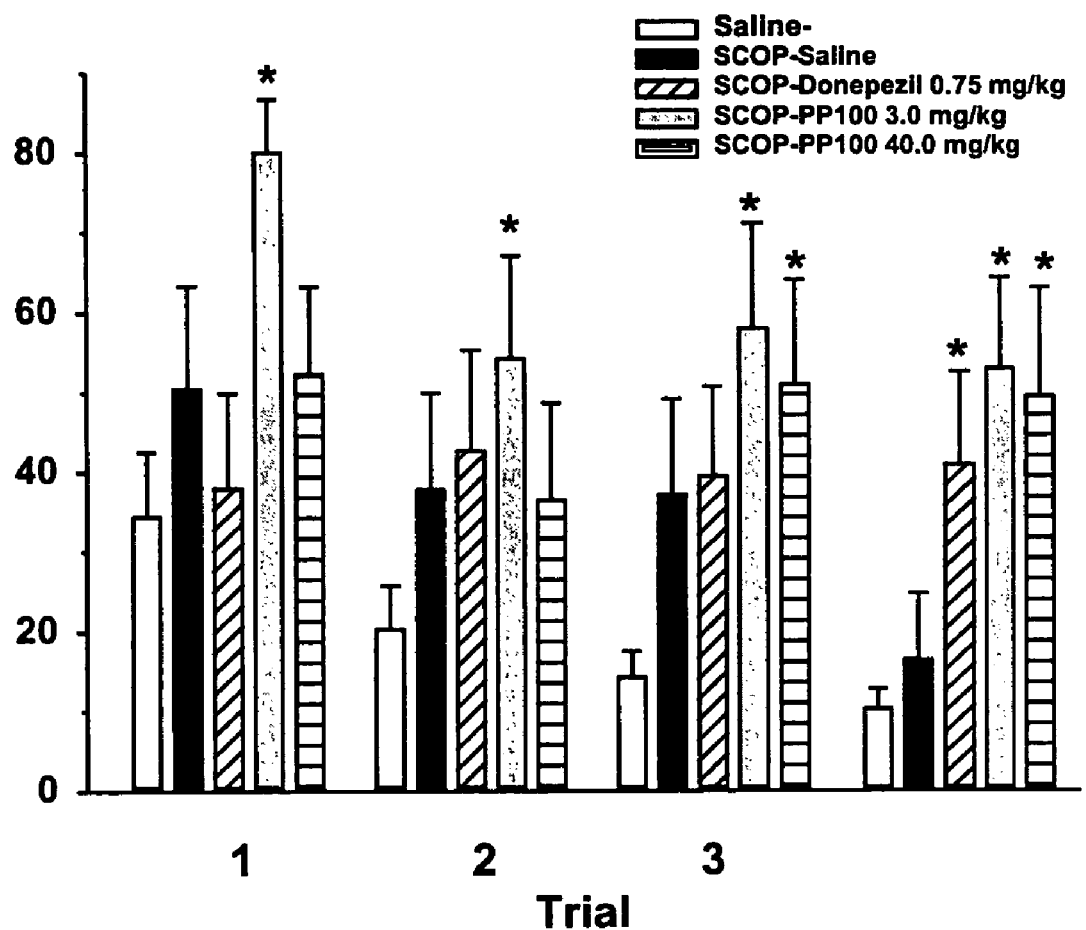
FIG. 1. Mean latency in seconds (±s.e.m.) to locate a highly visible platform by the various groups in the watermaze pre-test, over 4 trials. *=$p<0.05$ vs. Saline-Saline by post-hoc Fischer's LSD test following overall significant two-way repeated measures ANOVA. N=10 rats per group.

As used herein, the following terms and expressions have the indicated meanings. It will be appreciated that the compounds useful in the present invention can contain asymmetrically substituted carbon atoms, and can be isolated in optically active or racemic forms. It is well known in the art how to prepare optically active forms, such as by resolution of racemic forms or by synthesis, from optically active starting materials.

All chiral, diastereomeric, racemic forms and all geometric isomeric forms of a structure are intended, unless the specific stereochemistry or isomeric form is specifically indicated. The processes to prepare or manufacture compounds useful in the present invention are contemplated to be practiced on at least a multigram scale, kilogram scale, multikilogram scale, or industrial scale. Multigram scale, as used herein, is preferably the scale wherein at least one starting material is present in 10 grams or more, more preferably at least 50 grams or more, even more preferably at least 100 grams or more. Multi-kilogram scale, as used herein, is intended to mean the scale wherein more than one kilogram of at least one starting material is used. Industrial scale as used herein is intended to mean a scale which is other than a laboratory scale and which is sufficient to supply product sufficient for either clinical tests or distribution to consumers.

One diastereomer of a compound disclosed herein may display superior activity compared with the other. When required, separation of the racemic material can be achieved by HPLC using a chiral column or by a resolution using a resolving agent such as camphonic chloride as in Tucker, et al., *J. Med. Chem.*, 37:2437 (1994). A chiral compound described herein may also be directly synthesized using a chiral catalyst or a chiral ligand, e.g. Huffman, et al., *J. Org. Chem.*, 60:1590 (1995).

The present invention is intended to include all isotopes of atoms occurring on the compounds useful in the present invention. Isotopes include those atoms having the same atomic number but different mass numbers. By way of general example and without limitation, isotopes of hydrogen include tritium and deuterium. Isotopes of carbon include C-13 and C-14.

DEFINITIONS

As used herein, "cognition" refers to the mental process characterized by knowing, thinking, learning, understanding, and judging. See, e.g., Mosby's Medical Dictionary, $5^{th}$ edition (1998).

As used herein, "cognitive" refers to the mental process of comprehension, judgment, memory, and reasoning, as contrasted with emotional and volitional processes. See, e.g., Mosby's Medical Dictionary, $5^{th}$ edition (1998).

As used herein, "cognitive function" refers to an intellectual process by which one becomes aware of, perceives, or comprehends ideas. It involves all aspects of perception, thinking, reasoning, and remembering. See, e.g., Mosby's Medical Dictionary, $5^{th}$ edition (1998).

As used herein, "cognitive dysfunction" refers to an abnormal or detective cognitive function. Typical cognitive dysfunctions include, e.g., dementia, age-related deficit in cognitive performance, stress-related deficit in cognitive performance, mild cognitive impairment (MCI), schizophrenia, Alzheimer's disease (AD), and memory related disorders. Other cognitive dysfunctions include those that are related to Down's syndrome, central nervous system (CNS) disorders, peripheral nervous system (PNS) disorders, memory related disorders, learning and behavior disorders, cognition impairment, impairment of PNS functions, impairments of CNS functions, and impairment of memory and related functions.

As used herein, "cognitive performance" refers to the ability or capacity of an individual to comprehend, judge, memorize, and reason. The cognitive performance is the capacity of an individual to become aware of, perceive, or comprehend ideas.

As used herein, "mild cognitive impairment" or "MCI" refers to isolated episodic memory decline.

As used herein, "dementia" is an umbrella term for several symptoms related to a decline in thinking skills. Dementia refers to a general mental deterioration due to organic or psychological factors; characterized by disorientation, impaired memory, judgment, and intellect, and a shallow labile effect. Common symptoms include a gradual loss of memory, problems with reasoning or judgment, disorientation, difficulty in learning, loss of language skills, and decline in the ability to perform routine tasks. People with dementia typically experience changes in their personalities and behavioral problems, such as agitation, anxiety, delusions (believing in a reality that does not exist), and hallucinations (seeing things that do not exist). Specific types of dementia include, e.g., vascular dementia (VaD), dementia of the Alzheimer's type, dementia due to HIV disease, dementia due to head trauma, dementia due to Parkinson's disease, dementia due to Huntington's disease, dementia due to Pick's disease, dementia due to Creutzfeldt-Jacob disease, substance-induced persisting dementia, dementia due to multiple etiologies, and global dementia. See, e.g., Diagnostic and Statistical Manual of Mental Disorders, $4^{th}$ edition, Text Revision (DSM-IV-TR) (2000).

As used herein, "dementia of the Alzheimer's type," "Alzheimer's disease," or "AD" refers to a general mental deterioration due to organic or psychological factors; characterized by disorientation, impaired memory, judgment, and intellect, and a shallow labile effect. See, e.g., Stedman's Medical Dictionary, $11^{th}$ edition (1990). Alzheimer's disease (AD) is a progressive, degenerative disease of the brain and is one of several disorders that cause the gradual loss of brain cells. Specific types of dementia of the Alzheimer's type include, e.g., dementia of the Alzheimer's type without behavioral disturbance, dementia of the Alzheimer's type with behavior disturbance, dementia of the Alzheimer's type with early onset, and dementia of the Alzheimer's type with late onset. See, e.g., Diagnostic and Statistical Manual of Mental Disorders, $4^{th}$ edition, Text Revision (DSM-IV-TR) (2000).

As used herein, "down syndrome" refers to a congenital condition characterized by varying degrees of mental retardation and multiple defects. It is the most common chromosomal abnormality of a generalized syndrome and is caused by the presence of an extra chromosome 21 in the G group or, in a small percent of cases, by the translocation of chromosome 14 or 15 in the D group and chromosomes 21 or 22. See, e.g., Mosby's Medical Dictionary, $5^{th}$ edition (1998).

As used herein, "central nervous system (CNS) disorders" refers to Alzheimer's disease, Down syndrome, Parkinson's disease and disorders related to M1 and M2 receptors.

As used herein, "peripheral nervous system (PNS) disorders" refers to muscular weakness, muscle wastage, muscular cramps, muscle spasticity, which later causes joint or skeletal deformities, loss of coordination, muscle pain, skin rash, pins and needles, breathing difficulties, swallowing difficulties. PNS disorders also include inflammatory myopathies, diseases of the neuromuscular junction, some of the different diseases of the neuromuscular junction that include Guillain-Barre syndrome, myasthenia gravis and polyneuropathy. PNS disorders also include acquired nerve diseases such as polyneuropathies, which can be triggered by certain drugs (e.g., chemotherapeutic agents and medications for lowering blood cholesterol), dietary deficiencies (e.g., vitamin B12) and hormonal disorders (e.g., diabetes and hypothyroidism). PNS disorders also include compression neuropathies, where nerves may become compressed by other structures and tissues (such as bones), leading to impairment of function and symptoms such as pain, numbness and tingling. Some of the different types of compression neuropathies include carpal tunnel syndrome and sciatica. PNS disorders also include metabolic diseases where the muscles can't use certain crucial nutrients and this affects their functioning. Some of the metabolic diseases of muscle include phosphofructokinase deficiency, acid maltase deficiency and carnitine deficiency. PNS disorders also include cardio vascular system related, respiratory tract related, gastrointestinal tract related, urinary tract related, biliary tract related, and sweat gland related disorders.

As used herein, "memory related disorders" refers to age associated memory disorder, Alzheimer's disease related memory disorder, loss of memory, lack of concentration, lack of understanding, lack of cognition, and lack of learning ability.

As used herein, "improvement in learning and behavior" refers to an increase in the ability or capacity of an individual to learn and behave; and can be measured by tests typically employed by those of skill in the art. Such an improvement can include at least about a 10% increase, at least about a 25% increase, or at least about a 50% increase.

As used herein, "improvement in cognition" refers to an increase in the ability or capacity of an individual to comprehend, judge, memorize, and reason; and can be measured by tests typically employed by those of skill in the art. Such an improvement can include at least about a 10% increase, at least about a 25% increase, or at least about a 50% increase.

As used herein, "enhancements of PNS functions" refers to an increase in the peripheral nervous system functions; and can be measured by tests typically employed by those of skill in the art. Such an improvement can include at least about a 10% increase, at least about a 25% increase, or at least about a 50% increase.

As used herein, "enhancements of CNS functions" refers to an increase in the central nervous system functions; and can be measured by tests typically employed by those of skill in the art. Such an improvement can include at least about a 10% increase, at least about a 25% increase, or at least about a 50% increase.

As used herein, "enhancements of memory and related functions" refers to an increase in the ability or capacity of an individual to remember or memorize; and can be measured by tests typically employed by those of skill in the art. Such an improvement can include at least about a 10% increase, at least about a 25% increase, or at least about a 50% increase.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the compounds useful in the present invention can be synthesized from the parent compound, which contains a basic or acidic moiety, by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences*, 17th ed., Mack Publishing Company, Easton, Pa., p. 1418 (1985), the disclosure of which is hereby incorporated by reference.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication commensurate with a reasonable benefit/risk ratio.

"Stable compound" and "stable structure" are meant to indicate a compound that is sufficiently robust to survive isolation to a useful degree of purity from a reaction mixture, and formulation into an efficacious therapeutic agent. Only stable compounds are contemplated by the present invention.

"Substituted" is intended to indicate that one or more hydrogens on the atom indicated in the expression using "substituted" is replaced with a selection from the indicated group(s), provided that the indicated atom's normal valency is not exceeded, and that the substitution results in a stable compound. Suitable indicated groups include, e.g., alkyl, alkoxy, halo, haloalkyl, hydroxy, hydroxyalkyl, aryl, heteroaryl, heterocycle, cycloalkyl, alkanoyl, alkoxycarbonyl, amino, alkylamino, acylamino, nitro, trifluoromethyl, trifluoromethoxy, carboxy, carboxyalkyl, keto, thioxo, alkylthio, alkylsulfinyl, alkylsulfonyl and cyano. When a substituent is keto (i.e., =O) or thioxo (i.e., =S) group, then 2 hydrogens on the atom are replaced.

"Therapeutically effective amount" is intended to include an amount of a compound useful in the present invention or an amount of the combination of compounds claimed, e.g., to treat or prevent cognitive dysfunctions or treat the symptoms of cognitive dysfunctions in a host. The combination of compounds is preferably a synergistic combination. Synergy, as described for example by Chou and Talalay, *Adv. Enzyme Regul.*, 22:27 (1984), occurs when the effect (in this case, treatment or prevention of cognitive dysfunctions) of the compounds when administered in combination is greater than the additive effect of the compounds when administered alone as a single agent. In general, a synergistic effect is most clearly demonstrated at suboptimal concentrations of the compounds. Synergy can be in terms of lower cytotoxicity, increased activity, or some other beneficial effect of the combination compared with the individual components.

"Prodrugs" are intended to include any covalently bonded substances which release the active parent drug or other formulas or compounds of the present invention in vivo when such prodrug is administered to a mammalian subject. Prodrugs of a compound of the present invention, for example stearyl choline chloride, are prepared by modifying functional groups present in the compound in such a way that the modifications are cleaved, either in routine manipulation in vivo, to the parent compound. Prodrugs include compounds of the present invention wherein the hydroxy or amino group is bonded to any group that, when the prodrug is administered to a mammalian subject, cleaves to form a free hydroxyl or free amino, respectively. Examples of prodrugs include, but are not limited to, acetate, formate and benzoate derivatives of alcohol and amine functional groups in the compounds of the present invention, and the like.

"Metabolite" refers to any substance resulting from biochemical processes by which living cells interact with the active parent drug or other formulas or compounds of the present invention in vivo, when such active parent drug or other formulas or compounds of the present are administered to a mammalian subject. Metabolites include products or intermediates from any metabolic pathway.

"Metabolic pathway" refers to a sequence of enzyme-mediated reactions that transform one compound to another and provide intermediates and energy for cellular functions. The metabolic pathway can be linear or cyclic. A specific metabolic pathway includes the hydrolase mediated hydrolysis of esters into carboxylic acids.

The term "alkyl" refers to a monoradical branched or unbranched saturated hydrocarbon chain preferably having from 1 to 40 carbon atoms, more preferably 1 to 30 carbon atoms, and even more preferably 1 to 26 carbon atoms. This term is exemplified by groups such as methyl, ethyl, n-propyl, iso-propyl, n-butyl, iso-butyl, sec-butyl, n-hexyl, n-decyl, tetradecyl, stearyl, octyl, decyl, lauryl, myristyl, palmityl, and the like.

The alkyl can optionally be substituted with one or more alkoxy, halo, haloalkyl, hydroxy, hydroxyalkyl, aryl, heteroaryl, heterocycle, cycloalkyl, alkanoyl, alkoxycarbonyl, amino, alkylamino, acylamino, nitro, trifluoromethyl, trifluoromethoxy, carboxy, carboxyalkyl, keto, thioxo, alkylthio, alkylsulfinyl, alkylsulfonyl, cyano, $NR_xR_x$ or $COOR_x$, wherein each $R_x$ is independently H or alkyl.

The alkyl can optionally be interrupted with one or more non-peroxide oxy (—O—), thio (—S—), sulfonyl (SO) or sulfoxide ($SO_2$).

The alkyl can optionally be at least partially unsaturated, thereby providing an alkenyl or alkynyl.

The term "alkylene" refers to a diradical branched or unbranched saturated hydrocarbon chain preferably having from 1 to 40 carbon atoms, more preferably 1 to 10 carbon atoms, and even more preferably 1 to 6 carbon atoms. This term is exemplified by groups such as methylene, ethylene, n-propylene, iso-propylene, n-butylene, iso-butylene, sec-butylene, n-hexylene, n-decylene, tetradecylene, and the like.

The alkylene can optionally be substituted with one or more alkoxy, halo, haloalkyl, hydroxy, hydroxyalkyl, aryl, heteroaryl, heterocycle, cycloalkyl, alkanoyl, alkoxycarbonyl, amino, alkylamino, acylamino, nitro, trifluoromethyl, trifluoromethoxy, carboxy, carboxyalkyl, keto, thioxo, alkylthio, alkylsulfinyl, alkylsulfonyl and cyano.

The term "alkoxy" refers to the groups alkyl-O—, where alkyl is defined herein. Preferred alkoxy groups include, e.g., methoxy, ethoxy, n-propoxy, iso-propoxy, n-butoxy, tert-butoxy, sec-butoxy, n-pentoxy, n-hexoxy, 1,2-dimethylbutoxy, and the like.

The alkyoxy can optionally be substituted with one or more alkyl, halo, haloalkyl, hydroxy, hydroxyalkyl, aryl, heteroaryl, heterocycle, cycloalkyl, alkanoyl, alkoxycarbonyl, amino, alkylamino, acylamino, nitro, trifluoromethyl, trifluoromethoxy, carboxy, carboxyalkyl, keto, thioxo, alkylthio, alkylsulfinyl, alkylsulfonyl and cyano.

The term "aryl" refers to an unsaturated aromatic carbocyclic group of from 6 to 20 carbon atoms having a single ring (e.g., phenyl) or multiple condensed (fused) rings, wherein at least one ring is aromatic (e.g., naphthyl, dihydrophenanthrenyl, fluorenyl, or anthryl). Preferred aryls include phenyl, naphthyl and the like.

The aryl can optionally be substituted with one or more alkyl, alkoxy, halo, haloalkyl, hydroxy, hydroxyalkyl, heteroaryl, heterocycle, cycloalkyl, alkanoyl, alkoxycarbonyl, amino, alkylamino, acylamino, nitro, trifluoromethyl, trifluoromethoxy, carboxy, carboxyalkyl, keto, thioxo, alkylthio, alkylsulfinyl, alkylsulfonyl and cyano.

The term "cycloalkyl" refers to cyclic alkyl groups of from 3 to 20 carbon atoms having a single cyclic ring or multiple condensed rings. Such cycloalkyl groups include, by way of example, single ring structures such as cyclopropyl, cyclobutyl, cyclopentyl, cyclooctyl, and the like, or multiple ring structures such as adamantanyl, and the like.

The cycloalkyl can optionally be substituted with one or more alkyl, alkoxy, halo, haloalkyl, hydroxy, hydroxyalkyl, aryl, heteroaryl, heterocycle, alkanoyl, alkoxycarbonyl, amino, alkylamino, acylamino, nitro, trifluoromethyl, trifluoromethoxy, carboxy, carboxyalkyl, keto, thioxo, alkylthio, alkylsulfinyl, alkylsulfonyl and cyano.

The cycloalkyl can optionally be at least partially unsaturated, thereby providing a cycloalkenyl.

The term "halo" refers to fluoro, chloro, bromo, and iodo. Similarly, the term "halogen" refers to fluorine, chlorine, bromine, and iodine.

"Haloalkyl" refers to alkyl as defined herein substituted by 1-4 halo groups as defined herein, which may be the same or different. Representative haloalkyl groups include, by way of example, trifluoromethyl, 3-fluorododecyl, 12,12,12-trifluorododecyl, 2-bromooctyl, 3-bromo-6-chloroheptyl, and the like.

The term "heteroaryl" is defined herein as a monocyclic, bicyclic, or tricyclic ring system containing one, two, or three aromatic rings and containing at least one nitrogen, oxygen, or sulfur atom in an aromatic ring, and which can be unsubstituted or substituted, for example, with one or more, and in particular one to three, substituents, like halo, alkyl, hydroxy, hydroxyalkyl, alkoxy, alkoxyalkyl, haloalkyl, nitro, amino, alkylamino, acylamino, alkylthio, alkylsulfinyl, and alkylsulfonyl. Examples of heteroaryl groups include, but are not limited to, 2H-pyrrolyl, 3H-indolyl, 4H-quinolizinyl, 4nH-carbazolyl, acridinyl, benzo[b]thienyl, benzothiazolyl, β-carbolinyl, carbazolyl, chromenyl, cinnaolinyl, dibenzo[b,d] furanyl, furazanyl, furyl, imidazolyl, imidizolyl, indazolyl, indolisinyl, indolyl, isobenzofuranyl, isoindolyl, isoquinolyl, isothiazolyl, isoxazolyl, naphthyridinyl, naptho[2,3-b], oxazolyl, perimidinyl, phenanthridinyl, phenanthrolinyl, phenarsazinyl, phenazinyl, phenothiazinyl, phenoxathiinyl, phenoxazinyl, phthalazinyl, pteridinyl, purinyl, pyranyl, pyrazinyl, pyrazolyl, pyridazinyl, pyridyl, pyrimidinyl, pyrimidinyl, pyrrolyl, quinazolinyl, quinolyl, quinoxalinyl, thiadiazolyl, thianthrenyl, thiazolyl, thienyl, triazolyl, and xanthenyl. In one embodiment the term "heteroaryl" denotes a monocyclic aromatic ring containing five or six ring atoms containing carbon and 1, 2, 3, or 4 heteroatoms independently selected from the group non-peroxide oxygen, sulfur, and N(Z) wherein Z is absent or is H, O, alkyl, phenyl or benzyl. In another embodiment heteroaryl denotes an ortho-fused bicyclic heterocycle of about eight to ten ring atoms derived therefrom, particularly a benz-derivative or one derived by fusing a propylene, or tetramethylene diradical thereto.

The heteroaryl can optionally be substituted with one or more alkyl, alkoxy, halo, haloalkyl, hydroxy, hydroxyalkyl, aryl, heterocycle, cycloalkyl, alkanoyl, alkoxycarbonyl, amino, alkylamino, acylamino, nitro, trifluoromethyl, trifluoromethoxy, carboxy, carboxyalkyl, keto, thioxo, alkylthio, alkylsulfinyl, alkylsulfonyl and cyano.

The term "heterocycle" refers to a saturated or partially unsaturated ring system, containing at least one heteroatom selected from the group oxygen, nitrogen, and sulfur, and optionally substituted with alkyl or $C(=O)OR^b$, wherein $R^b$ is hydrogen or alkyl. Typically heterocycle is a monocyclic, bicyclic, or tricyclic group containing one or more heteroatoms selected from the group oxygen, nitrogen, and sulfur. A heterocycle group also can contain an oxo group (=O) attached to the ring. Non-limiting examples of heterocycle groups include 1,3-dihydrobenzofuran, 1,3-dioxolane, 1,4-dioxane, 1,4-dithiane, 2H-pyran, 2-pyrazoline, 4H-pyran, chromanyl, imidazolidinyl, imidazolinyl, indolinyl, isochromanyl, isoindolinyl, morpholine, piperazinyl, piperidine, piperidyl, pyrazolidine, pyrazolidinyl, pyrazolinyl, pyrrolidine, pyrroline, quinuclidine, and thiomorpholine.

The heterocycle can optionally be substituted with one or more alkyl, alkoxy, halo, haloalkyl, hydroxy, hydroxyalkyl, aryl, heterocycle, cycloalkyl, alkanoyl, alkoxycarbonyl, amino, alkylamino, acylamino, nitro, trifluoromethyl, trifluoromethoxy, carboxy, carboxyalkyl, keto, thioxo, alkylthio, alkylsulfinyl, alkylsulfonyl and cyano.

Examples of nitrogen heterocycles and heteroaryls include, but are not limited to, pyrrole, imidazole, pyrazole, pyridine, pyrazine, pyrimidine, pyridazine, indolizine, isoindole, indole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, morpholino, piperidinyl, tetrahydrofuranyl, and the like as well as N-alkoxy-nitrogen containing heterocycles.

Another class of heterocyclics is known as "crown compounds" which refers to a specific class of heterocyclic compounds having one or more repeating units of the formula $[-(CH_2-)_a A-]$ where a is equal to or greater than 2, and A at each separate occurrence can be O, N, S or P. Examples of crown compounds include, by way of example only, $[-(CH_2)_3-NH-]_3$, $[-((CH_2)_2-O)_4-((CH_2)_2-NH)_2]$ and the like. Typically such crown compounds can have from 4 to 10 heteroatoms and 8 to 40 carbon atoms.

The term "alkanoyl" refers to $C(=O)R$, wherein R is an alkyl group as previously defined.

The term "alkoxycarbonyl" refers to $C(=O)OR$, wherein R is an alkyl group as previously defined.

The term "amino" refers to $-NH_2$, and the term "alkylamino" refers to $-NR_2$, wherein at least one R is alkyl and the second R is alkyl or hydrogen. The term "acylamino" refers to $RC(=O)N$, wherein R is alkyl or aryl.

The term "nitro" refers to $-NO_2$.
The term "trifluoromethyl" refers to $-CF_3$.
The term "trifluoromethoxy" refers to $-OCF_3$.
The term "cyano" refers to $-CN$.
The term "hydroxy" refers to $-OH$.

As to any of the above groups, which contain one or more substituents, it is understood, of course, that such groups do not contain any substitution or substitution patterns which are sterically impractical and/or synthetically non-feasible. In addition, the compounds of this invention include all stereochemical isomers arising from the substitution of these compounds.

Selected substituents within the compounds described herein are present to a recursive degree. In this context, "recursive substituent" means that a substituent may recite another instance of itself. Because of the recursive nature of such substituents, theoretically, a large number may be present in any given claim. One of ordinary skill in the art of medicinal chemistry understands that the total number of such substituents is reasonably limited by the desired properties of the compound intended. Such properties include, by of example and not limitation, physical properties such as molecular weight, solubility or log P, application properties such as activity against the intended target, and practical properties such as ease of synthesis.

Recursive substituents are an intended aspect of the invention. One of ordinary skill in the art of medicinal chemistry understands the versatility of such substituents. To the degree that recursive substituents are present in a claim of the invention, the total number will be determined as set forth above.

As used herein, "treating" or "treat" includes (i) preventing a pathologic condition (e.g., AD) from occurring (e.g. prophylaxis); (ii) inhibiting the pathologic condition (e.g., AD) or arresting its development; and (iii) relieving the pathologic condition (e.g., AD).

As used herein, "one or more" refers to a whole integer, being at least one. Specifically, one or more includes, e.g., 1, 2, 3, 4, or 5.

Compounds described herein may be effective for the treatment of cognitive dysfunctions, when administered in combination with neurotransmitter precursors such as phenylalanine, tyrosine and/or tryptophan. See, WO 01/26623. A compound described herein may be effective for the treatment of cognitive dysfunctions when administered in combination with a neurotransmitter precursor. Compounds described herein may be effective for the treatment of cognitive dysfunctions, when administered in combination with other active compounds such as Coenzyme Q10, *Ginkgo biloba*, Huperzine A, Phosphatidylserine, Vitamin E, Tacrine (Cognex®), Donepezil (Aricept®), Rivastigmine (Exelon®)), NAMENDA (memantine hydrochloride) and/or Galantamine (Reminyl®).

Coenzyme Q10

Coenzyme Q10, or ubiquinone, is an antioxidant that occurs naturally in the body and is needed for normal cell reactions to occur. A synthetic version of this compound, called idebenone, can also be used in the methods described herein.

*Ginkgo Biloba*

*Ginkgo biloba* is a plant extract containing several compounds that may have positive effects on cells within the brain and the body. *Ginkgo biloba* is thought to have both antioxidant and anti-inflammatory properties, to protect cell membranes, and to regulate neurotransmitter function. *Ginkgo* has been used for centuries in traditional Chinese medicine and currently is being used in Europe to alleviate cognitive symptoms associated with a number of neurological conditions.

In a study published in the *Journal of the American Medical Association* (Oct. 22/29, 1997), Pierre L. Le Bars, MD, PhD, of the New York Institute for Medical Research, and his colleagues observed in some participants a modest improvement in cognition, activities of daily living (such as eating and dressing), and social behavior. The researchers found no measurable difference in overall impairment.

Results from this study show that ginkgo may help some individuals with Alzheimer's disease. Few side effects are associated with the use of *Ginkgo*, but it is known to reduce the ability of blood to clot, potentially leading to more serious conditions, such as internal bleeding. This risk may increase if *Ginkgo biloba* is taken in combination with other blood-thinning drugs, such as aspirin and warfarin.

Huperzine A

Huperzine A is a moss extract that has been used in traditional Chinese medicine for centuries. Because it has properties similar to those of FDA-approved Alzheimer medications, it is promoted as a treatment for Alzheimer's disease.

Evidence shows that the effectiveness of huperzine A may be comparable to that of the approved drugs. Alzheimer's Association website, Oct. 31, 2002 (http://www.alz.org).

Phosphatidylserine

Phosphatidylserine is a kind of lipid, or fat, that is the primary component of cell membranes of neurons. In Alzheimer's disease and similar disorders, neurons degenerate for reasons that are not yet understood. The strategy behind the possible treatment with phosphatidylserine is to shore up the cell membrane and possibly protect cells from degenerating. Alzheimer's Association website, Oct. 31, 2002 (http://www.alz.org).

Vitamin E

Vitamin E supplements are often prescribed as a treatment for Alzheimer's disease, because they may help brain cells defend themselves from "attacks." Normal cell functions create a byproduct a called free radical, a kind of oxygen molecule that can damage cell structures and genetic material. This damage, called oxidative stress, may play a role in Alzheimer's disease.

Cells have natural defenses against this damage, including the antioxidants vitamins C and E, but with age some of these natural defenses decline. Research has shown that taking vitamin E supplements may offer some benefit to people with Alzheimer's.

Most people can take vitamin E without side effects. A person taking "blood-thinners," however, may not be able to take Vitamin E or will need to be monitored closely by a physician.

Cholinesterase Inhibitors

Currently, there are four drugs approved by the U.S. Food and Drug Administration (FDA) for the treatment of Alzheimer's disease: Tacrine (Cognex®), Donepezil (Aricept®), Rivastigmine (Exelon®), and Galantamine (Reminyl®). These four medications are in a class of drugs known as cholinesterase inhibitors. They are designed to prevent the breakdown of acetylcholine, a chemical messenger in the brain that is important for memory and other thinking skills. The drugs work to keep levels of the chemical messenger high, even while the cells that produce the messenger continue to become damaged or die. About half of the people who take cholinesterase inhibitors experience a modest improvement in cognitive symptoms.

As used herein, Tacrine (Cognex®) refers to 1,2,3,4-tetrahydro-9-acridinamine or 9-amino-1,2,3,4-tetrahydro-5-aminoacridine. See, e.g., Merck Index (11$^{th}$ edition) and *N. Engl. J. Med.*, 315:1241 (1986). Tacrine (Cognex®) is shown below:

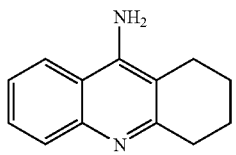

As used herein, Donepezil (Aricept®) refers to (±)-2-[(1-benzyl-4-piperidyl)methyl]-5,6-dimethoxy-1-indanone hydrochloride. See, e.g., USP Dictionary (2000 edition). Donepezil (Aricept®) is shown below:

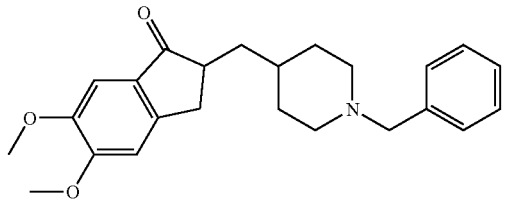

As used herein, Rivastigmine (Exelon®) refers to (S)-3-[1-(dimethylamino)ethyl]phenyl ethylmethylcarbamate. See, e.g., USP Dictionary (2000 edition). Rivastigmine (Exelon®) is shown below:

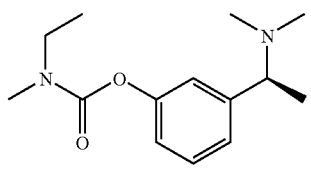

As used herein, Galanthamine (Reminyl®) refers to 4a,5,9,10,11,12-hexahydro-3-methoxy-11-methyl-6H-benzofuro[3a,3,2-ef][2]benzazepin-6-ol. See, e.g., Merck Index (11$^{th}$ edition) and *J. Chem. Soc.* 806 (1962). Galanthamine (Reminyl®) is shown below:

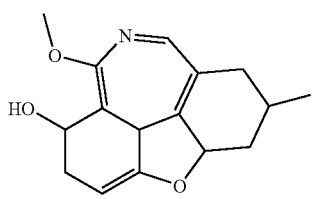

NAMENDA (Memantine Hydrochloride)

As used herein, NAMENDA (memantine hydrochloride) is an orally active NMDA receptor antagonist. The chemical name for memantine hydrochloride is 1-amino-3,5-dimethyladamantane hydrochloride, and is shown below:

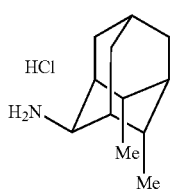

Other features of the invention will become apparent in the course of the following descriptions of exemplary embodiments, which are given for illustration of the invention and are not intended to be limiting thereof.

Specific values, ranges, substituents, and embodiments provided below are for illustration purposes only, and do not otherwise the scope of the invention, which is defined by the claims.

Choline Esters:

Suitable choline esters useful in the present invention include, e.g., compounds of formula (I):

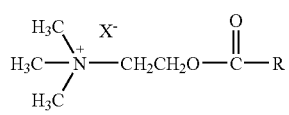

(I)

wherein,

R is a straight-chain or branched chain alkyl, alkoxy, haloalkyl, hydroxyalkyl, aryl, heteroaryl, heterocycle, cycloalkyl, alkylamino, trifluoromethyl, trifluoromethoxy, alkylthio, alkylsulfinyl, or alkylsulfonyl; and X is a pharmaceutically acceptable counterion; or a pharmaceutically acceptable salt thereof.

Suitable counterions include, e.g., fluoride, chloride, bromide, iodide, sulfate, nitrate, perchlorate, phosphate, acetate, benzoate, tartrate, citrate, propionate, gluconate, lactate, maleate, fumarate, benzylate, camsylate, esylate, glucepate, mesylate, napsylate, an organic carboxylic acid salt, and the like.

Specifically, R can be alkyl. More specifically, R can be a linear alkyl. More specifically, R can be $-(CH_2)_{16}-CH_3$. Alternatively, R can be a branched alkyl. Alternatively, R can be a fatty acid residue having from about 6 to about 26 carbon atoms, usually from about 16 to about 24 carbon atoms, and can be saturated, partially unsaturated, or unsaturated; such as palmitic acid, palmitoleic acid, stearic acid, oleic acid, linoleic acid, eicosenoic acid, arachidonic acid, docosahexaenoic acid, eicosapentaenoic acid, linolenic acid, caprylic acid, mixtures thereof or the like.

Specifically, X can be F, Cl, Br or I.

A specific compound of formula (I) includes stearyl choline chloride or choline stearate chloride, as shown below:

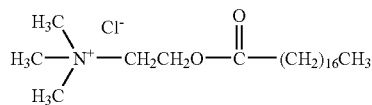

The present invention also provides for a method of treating cognitive dysfunctions in a mammal that include administering an effective amount of choline ester to a mammal.

The choline ester can be substantially free of bodily fluids. For example, the choline ester can include less than about 10 wt. % bodily fluids, less than about 5 wt. % bodily fluids, or less than about 1 wt. % bodily fluids.

The choline ester can be substantially pure. For example, the choline ester can be at least 90 wt. % pure, at least 95 wt. % pure, at least 98 wt. % pure or at least 99 wt. % pure.

The choline ester can exist in a unit dosage form (e.g., pill, tablet, or capsule). Additionally, the choline ester, together with a pharmaceutically acceptable carrier or diluent, can form a pharmaceutical composition. Additionally, the choline ester, together with a micellar formulation or a liposomal formulation, can form a pharmaceutical composition.

Any patent, patent document, or reference disclosed herein is incorporated into reference into this invention and forms part of this invention.

Utility

The compounds disclosed herein (i.e., those useful in the present invention) possess suitable cognitive function enhancement activity and are therefore useful as agents for the treatment of cognitive dysfunctions and related diseases and symptoms.

The compounds disclosed herein are also useful as standard or reference compounds for use in tests or assays for determining the ability of an agent to treat, prevent, or lessen the conditions or symptoms associated with cognitive dysfunction, for example in a pharmaceutical research program. Thus, the compounds disclosed herein may be used as control or reference compound in such assays and as a quality control standard. The compounds of the present invention may be provided in a commercial kit or container for use as such standard or reference compound.

As used herein, "µg" denotes microgram, "mg" denotes milligram, "g" denotes gram, "µL" denotes microliter, "mL" denotes milliliter, "L" denotes liter, "nM" denotes nanomolar, "µM" denotes micromolar, "mM" denotes millimolar, "M" denotes molar and "nm" denotes nanometer. "Sigma" stands for the Sigma-Aldrich Corp. of St. Louis Mo.

Dosage and Formulation

The compounds of this invention can be administered as treatment for cognitive dysfunctions, and related diseases and symptoms, by any means that produces contact of the active agent with the agent's site of action in the body of a mammal. They can be administered by any conventional means available for use in conjunction with pharmaceuticals, either as individual therapeutic agents or in a combination of therapeutic agents. They can be administered alone, but preferably are administered with a pharmaceutical carrier selected on the basis of the chosen route of administration and standard pharmaceutical practice.

The dosage administered will, of course, vary depending upon known factors, such as the pharmacodynamic characteristics of the particular agent and its mode and route of administration; the age, health and weight of the recipient; the nature and extent of the symptoms; the kind of concurrent treatment; the frequency of treatment; and the effect desired. A daily dosage of active ingredient can be expected to be about 0.001 to about 1000 milligrams per kilogram of body weight, with the preferred dose being about 0.1 to about 100 mg/kg, preferably administered several times a day.

Dosage forms of compositions suitable for administration contain from about 20 mg to about 1000 mg of active ingredient per unit. In these pharmaceutical compositions the active ingredient will ordinarily be present in an amount of about 0.5-95% by weight based on the total weight of the composition. The active ingredient can be administered orally in solid dosage forms, such as capsules, tablets and powders, or in liquid dosage forms, such as elixirs, syrups and suspensions. It can also be administered parenterally, in sterile liquid dosage forms. Additives may also be included in the formulation to enhance the physical appearance, improve stability, and aid in disintegration after administration. For example, liquid dosage forms for oral administration can contain coloring and flavoring to increase patient acceptance.

Gelatin capsules contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours or days. Sustained release products can also be formulated for implantation or transdermal/transmucosal delivery.

Such formulations typically will include a polymer that biodegrades or bioerodes thereby releasing a portion of the active ingredient. The formulations may have the form of microcapsules, liposomes, solid monolithic implants, gels, viscous fluids, discs, or adherent films.

Compressed tablets can be sugar coated or film coated to mask any unpleasant taste and protect the tablet from the atmosphere, or enteric coated for selective disintegration in the gastrointestinal tract.

Film-coated tablets are compressed tablets, which are covered with as thin layer of film or water-soluble material. A number of polymeric substances with film-forming properties may be used. Film coating imparts the same general characteristics as sugar coating with the added advantage of a greatly reduced time period required for the coating operation.

Enteric-coated tablets are compressed tablets coated with substances that resist solution in gastric fluid but disintegrate in the intestine. Enteric coatings can be used for tablets containing drug substances which are inactivated or destroyed in the stomach, for those which irritate the mucosa, or as a means of delayed release of the medication.

Multiple compressed tablets are compressed tablets made by more than one compression cycle.

Layered tablets are prepared by compressing additional tablet granulation on a previously compressed granulation. The operation may be repeated to produce multilayered tablets of two or three layers. Special tablet presses are required to make layered tablets.

Press-coated tablets, which are also referred to as dry-coated, are prepared by feeding previously compressed tablets into a special tableting machine and compressing another granulation layer around the preformed tablets. They have all the advantages of compressed tablets, i.e., slotting, monogramming, speed of disintegration, etc., while retaining the attributes of sugar-coated tablets in masking the taste of the drug substance in the core tablets. Press-coated tablets can also be used to separate incompatible drug substances; in addition, they can provide a means to give an enteric coating to the core tablets. Both types of multiple-compressed tablets have been widely used in the design of prolonged-action dosage forms.

Compressed tablets can be formulated to release the drug substance in a manner to provide medication over a period of time. There are a number of types which include delayed-action tablets in which the release of the drug substance is prevented for an interval of time after administration of until certain physiological conditions exist; repeat-action tablets which periodically release a complete dose of the drug substance to the gastrointestinal fluids; and the extended-release tablets which continuously release increments of the contained drug substance to the gastrointestinal fluids.

The non-aqueous carrier, or excipient, can be any substance that is biocompatible and liquid or soft enough at the mammal's body temperature to release the active ingredient into the animal's bloodstream at a desired rate. The carrier is usually hydrophobic and commonly organic, e.g., an oil or fat of vegetable, animal, mineral or synthetic origin or derivation. Preferably, but not necessarily, the carrier includes at least one chemical moiety of the kind that typifies "fatty" compounds, e.g., fatty acids, alcohols, esters, etc., i.e., a hydrocarbon chain, an ester linkage, or both. "Fatty" acids in this context include acetic, propionic and butyric acids through straight- or branched-chain organic acids containing up to 30 or more carbon atoms. Preferably, the carrier is immiscible in water and/or soluble in the substances commonly known as fat solvents. The carrier can correspond to a reaction product of such a "fatty" compound or compounds with a hydroxy compound, e.g., a mono-hydric, di-hydric, trihydric or other polyhydric alcohol, e.g., glycerol, propanediol, lauryl alcohol, polyethylene or -propylene glycol, etc. These compounds include the fat-soluble vitamins, e.g., tocopherols and their esters, e.g., acetates sometimes produced to stabilize tocopherols. Sometimes, for economic reasons, the carrier may preferably comprise a natural, unmodified vegetable oil such as sesame oil, soybean oil, peanut oil, palm oil, or an unmodified fat. Alternatively the vegetable oil or fat may be modified by hydrogenation or other chemical means which is compatible with the present invention. The appropriate use of hydrophobic substances prepared by synthetic means is also envisioned.

Typically, water, suitable oil, saline, aqueous dextrose (glucose), and related sugar solutions and glycols such as propylene glycol or polyethylene glycols are suitable carriers for parenteral solutions. Solutions for parenteral administration preferably contain a water-soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts, and sodium EDTA. In addition, parenteral solutions can contain preservatives, such as benzalkonium chloride, methyl- or propyl-paraben and chlorobutanol. Suitable pharmaceutical carriers are described in *Remington's Pharmaceutical Sciences*, supra, a standard reference text in this field.

In addition to the active or therapeutic ingredient, tablets contain a number of inert materials. The latter are known as additives or "adds." They may be classified according to the part they play in the finished tablet. The first group contains those which help to impart satisfactory compression characteristics to the formulation. These include (1) diluents, (2) binders, and (3) lubricants. The second group of added substances helps to give additional desirable physical characteristics to the finished tablet. Included in this group are (1) disintegrators, (2) colors, and in the case of chewable tablets, (3) flavors, and (4) sweetening agents.

Frequently the single dose of the active ingredient is small and an inert substance is added increase the bulk in order to make the tablet a practical size for compression. Diluents used for this purpose include dicalcium phosphate, calcium sulfate, lactose, kaolin, mannitol, sodium chloride, dry starch, and powdered sugar.

Most tablet formulators tend to use consistently only one or two diluents selected from the above group in their tablet formulations. Usually these have been selected on the basis of experience and cost factors. However, the compatibility of the diluent with the drug must be considered. When drug substances have low water solubility, it is recommended that water-soluble diluents be used to avoid possible bioavailability problems.

Agents used to impart cohesive qualities to the powdered material are referred to as binders or granulators. They impart a cohesiveness to the tablet formulation which insures the tablet remaining intact after compression, as well as improving the free-flowing qualities by the formulation of granules of desired hardness and size. Materials commonly used as binders include starch, gelatin, and sugars as sucrose, glucose, dextrose, molasses, and lactose. Natural and synthetic gums which have been used include acacia, sodium alginate, extract of Irish moss, panwar gum, ghatti gum, mucilage of isapol husks, carboxymethylcellulose, methylcellulose, polyvinylpyrrolidone, Beegum, and larch arabogalactan. Other agents which may be considered binders under certain circumstances are polyethylene glycol, ethylcellulose, waxes, water and alcohol.

The quality of binder used has considerable influence on the characteristics of the compressed tablets. The use of too much binder or too strong a binder will make a hard tablet which will not disintegrate easily. Alcohol and water are not binders in the true sense of the word; but because of their solvent action on some ingredients such as lactose and starch, they change the powdered material to granules and the residual moisture retained enables the materials to adhere together when compressed.

Lubricants have a number of functions in tablet manufacture. They improve the rate of flow of the tablet granulation, prevent adhesion of the tablet material to the surface of the dies and punches, reduce interparticle friction, and facilitate the ejection of the tablets from the die cavity. Commonly used lubricants include talc, magnesium stearate, calcium stearate, stearic acid, and hydrogenated vegetable oils. Most lubricants with the exception of talc are used in concentrations less than 1%. Lubricants are in most cases hydrophobic materials. Poor selection or excessive amounts can result in "waterproofing" the tablets, result in poor tablet disintegration and dissolution of the drug substance.

A disintegrator is a substance, or a mixture of substances, added to a tablet to facilitate its breakup or disintegration after administration. The active ingredient must be released from the tablet matrix as efficiently as possible to allow for its rapid dissolution. Materials serving as disintegrates have been chemically classified as starches, clays, celluloses, aligns, or gums.

The most popular disintegrators are corn and potato starch which have been well-dried and powdered. Starch has a great affinity for water and swells when moistened, thus facilitating the rupture of the tablet matrix. However, others have suggested that its disintegrating action in tablets is due to capillary action rather than swelling; the spherical shape of the starch grains increases the porosity of the tablet, thus promoting capillary action.

In addition to the starches a large variety of materials have been used and are reported to be effective as disintegrators. This group includes Veegum HV, methylcellulose, agar, bentonite, cellulose and wood products, natural sponge, cation-exchange resins, alginic acid, guar gum, citrus pulp, and carboxymethylcellulose. Sodium lauryl sulfate in combination with starch also has been demonstrated to be an effective disintegrant.

Colors in compressed tablets serve functions other than making the dosage from more esthetic in appearance. Any of the approved certified water-soluble FD&C dyes, mixtures of the same, or their corresponding lakes may be used to color tablets.

In addition to the sweetness which may be afforded by the diluent of the chewable tablet, e.g. mannitol or lactose, artificial sweetening agents may be included. Among the most promising are two derivatives of glycyrrhizin, the glycoside obtained from licorice.

Compressed tablets may be characterized or described by a number of specifications. These include the diameter size, shape, thickness, weight, hardness, and disintegration time.

Useful pharmaceutical dosage-forms for administration of the compounds of this invention can be illustrated as follows:

Capsules

A large number of unit capsules can be prepared by filling standard two-piece hard gelatin capsules each with 100 mg of powdered active ingredient, 150 mg of lactose, 50 mg of cellulose, and 6 mg magnesium stearic.

Soft Gelatin Capsules

A mixture of active ingredient in digestible oil such as soybean oil, cottonseed oil or olive oil can be prepared and injected by means of a positive displacement pump into gelatin to form soft gelatin capsules containing 100 mg of the active ingredient. The capsules should then be washed and dried.

Tablets

A large number of tablets can be prepared by conventional procedures so that the dosage unit is 100 mg of active ingredient, 0.2 mg of colloidal silicon dioxide, 5 milligrams of magnesium stearate, 275 mg of microcrystalline cellulose, 11 mg of starch and 98.8 mg of lactose.

Suspension

An aqueous suspension can be prepared for oral administration so that each 5 mL contain 25 mg of finely divided active ingredient, 200 mg of sodium carboxymethyl cellulose, 5 mg of sodium benzoate, 1.0 g of sorbitol solution, U.S.P., and 0.025 mg of vanillin.

Injectable

A parenteral composition suitable for administration by injection can be prepared by stirring 1.5% by weight of active ingredient in 10% by volume propylene glycol and water. The solution is sterilized by commonly used techniques.

Combination of Components (A) and (B)

Each therapeutic agent component useful in the present invention can independently be in any dosage form, such as those described above, and can also be administered in various ways, as described above. In the following description component (b) is to be understood to represent one or more agents as described previously. Thus, if components (a) and (b) are to be treated the same or independently, each agent of component (b) may also be treated the same or independently. Components (a) and (b) of the present invention may be formulated together, in a single dosage unit (that is, combined together in one capsule, tablet, powder, or liquid, etc.) as a combination product. When component (a) and (b) are not formulated together in a single dosage unit, the component (a) may be administered at the same time as component (b) or in any order; for example component (a) of this invention may be administered first, followed by administration of component (b), or they may be administered in the reverse order. If component (b) contains more that one agent, e.g., one antidepressant and one muscle relaxant, these agents may be administered together or separately in any order. When not administered at the same time, preferably the administration of component (a) and (b) occurs less than about one hour apart. Preferably, the route of administration of component (a) and (b) is oral.

The terms oral agent, oral compound, or the like, as used herein, denote compounds, which may be orally administered. Although it is preferable that component (a) and component (b) both be administered by the same route (that is, for example, both orally) or dosage form, if desired, they may each be administered by different routes (that is, for example, one component of the combination product may be administered orally, and another component may be administered intravenously) or dosage forms.

As is appreciated by a medical practitioner skilled in the art, the dosage of the combination therapy of the invention may vary depending upon various factors such as the pharmacodynamic characteristics of the particular agent and its mode and route of administration, the age, health and weight of the recipient, the nature and extent of the symptoms, the kind of concurrent treatment, the frequency of treatment, and the effect desired, as described above. The proper dosage of components (a) and (b) of the present invention will be readily ascertainable by a medical practitioner skilled in the art, based upon the present disclosure. By way of general guidance, typically a daily dosage may be about 100 milligrams to about 1.5 grams of each component. If component (b) represents more than one compound, then typically a daily dosage may be about 100 milligrams to about 1.5 grams of each agent of component (b). By way of general guidance, when the compounds of component (a) and component (b) are administered in combination, the dosage amount of each component may be reduced by about 70-80% relative to the usual dosage of the component when it is administered alone as a single agent for the treatment for cognitive dysfunctions, and related diseases and symptoms, in view of the synergistic effect of the combination.

The combination products of this invention may be formulated such that, although the active ingredients are combined in a single dosage unit, the physical contact between the active ingredients is minimized. In order to minimize contact, for example, where the product is orally administered, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. Another embodiment of this invention where oral administration is desired provides for a combination product wherein one of the active ingredients is coated with a sustained-release material which effects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low-viscosity grade of hydroxypropyl methylcellulose or other appropriate materials as known in the art, in order to further separate the active components. The polymer coating serves to form an additional barrier to interaction with the other component. In each formulation wherein contact is prevented between components (a) and (b) via a coating or some other material, contact may also be prevented between the individual agents of component (b).

Dosage forms of the combination products of the present invention wherein one active ingredient is enteric coated can be in the form of tablets such that the enteric coated component and the other active ingredient are blended together and then compressed into a tablet or such that the enteric coated component is compressed into one tablet layer and the other active ingredient is compressed into an additional layer. Optionally, in order to further separate the two layers, one or more placebo layers may be present such that the placebo layer is between the layers of active ingredients. In addition, dosage forms of the present invention can be in the form of capsules wherein one active ingredient is compressed into a tablet or in the form of a plurality of microtablets, particles, granules or non-perils, which are then enteric coated. These enteric coated microtablets, particles, granules or non-perils are then placed into a capsule or compressed into a capsule along with a granulation of the other active ingredient.

These as well as other ways of minimizing contact between the components of combination products of the present invention, whether administered in a single dosage form or administered in separate forms but at the same time or concurrently by the same manner, will be readily apparent to those skilled in the art, based on the present disclosure.

Pharmaceutical kits useful for the treatment for cognitive dysfunctions, and related diseases and symptoms, which include a therapeutically effective amount of a pharmaceutical composition that includes a compound of component (a) and one or more compounds of component (b), in one or more sterile containers, are also within the ambit of the present invention. Sterilization of the container may be carried out using conventional sterilization methodology well known to those skilled in the art. Component (a) and component (b) may be in the same sterile container or in separate sterile containers. The sterile containers of materials may comprise separate containers, or one or more multi-part containers, as desired. Component (a) and component (b), may be separate, or physically combined into a single dosage form or unit as described above. Such kits may further include, if desired, one or more of various conventional pharmaceutical kit components, such as for example, one or more pharmaceutically acceptable carriers, additional vials for mixing the components, etc., as will be readily apparent to those skilled in the art. Instructions, either as inserts or as labels, indicating quantities of the components to be administered, guidelines for administration, and/or guidelines for mixing the components, may also be included in the kit.

The following examples are introduced in order that the invention may be more readily understood. They are intended to illustrate the invention but not limit its scope.

This invention claims priority to PCT/US03/27062 filed on 29 Aug. 2003; and to U.S. Ser. No. 10/642,455 filed on 15 Aug. 2003; both of which are incorporated by reference herein, in their entirety.

EXAMPLES

The following prophetic examples illustrate orally administered solid dosage formulations that can be prepared to include the active ingredient as described herein (e.g., stearyl choline chloride).

Example 1

The active ingredient can be prepared as a controlled release pharmaceutical composition, as described in U.S. Pat. No. 6,491,950; wherein the active ingredient as described herein (e.g., stearyl choline chloride) is substituted for the active ingredient described therein. The composition can include a matrix of a material that includes a high melting point fatty acid ester, an oil, a polymeric cellulose derivative, or a combination thereof. The active ingredient can optionally be associated with the matrix. The formulation can optionally include a surfactant (e.g., polysorbate 80).

Suitable high melting fatty acid esters include, e.g., glyceryl behenate, glyceryl palmitostearate, and glyceryl stearate. Suitable oils include, e.g., corn oil, cottonseed oil, menhaden oil, safflower oil, sesame oil, shark-liver oil, soybean oil, olive oil, and wheat germ oil. Suitable cellulosic polymers include, e.g., a low-substituted hydroxypropyl ether cellulose polymer and a cellulosic polymer having methylether substitution. Suitable high melting fatty acid esters include, e.g., glyceryl behenate, glyceryl palmitostearate and glyceryl stearate.

Additional substances that can be included in the above pharmaceutical compositions, as well as methods to make the pharmaceutical compositions, are described in U.S. Pat. No. 6,491,950.

Example 2

The active ingredient can be prepared as a biphasic controlled release pharmaceutical composition, as described in U.S. Pat. No. 6,475,521; wherein the active ingredient as described herein (e.g., stearyl choline chloride) is substituted for the active ingredient described therein. Such a system can provide a dosage form that has prolonged gastric residence so that the active ingredient can be administered once daily to sustain a continuous plasma concentration of the active ingredient.

The controlled release pharmaceutical composition includes an inner solid particulate phase formed of substantially uniform granules containing the active ingredient, one or more hydrophilic polymers, and one or more hydrophobic polymers. The delivery system can also include one or more hydrophobic materials, such as one or more waxes, fatty alcohols and/or fatty acid esters. The controlled release pharmaceutical composition has an outer solid continuous phase in which the above granules of inner solid particulate phase are embedded and dispersed throughout. This outer solid continuous phase includes one or more hydrophilic polymers, one or more hydrophobic polymers and/or one or more hydrophobic materials such as one or more waxes, fatty alcohols and/or fatty acid esters. The controlled release pharmaceutical composition may be compressed into tablets or filled into capsules.

The particles of the inner solid particulate phase can include the active ingredient and an extended release material. The outer solid continuous phase can include an extended release material.

Additional substances that can be included in the above pharmaceutical compositions, as well as methods to make the pharmaceutical compositions, are described in U.S. Pat. No. 6,475,521.

Example 3

The active ingredient can be prepared as a controlled release tablet form, having a hydrophilic matrix that is suitable for the once-a-day administration, as described in U.S. Pat. No. 6,419,953; wherein the active ingredient of the present invention (e.g., stearyl choline chloride) is substituted for the active ingredient described therein. The tablet can include from about 50 weight percent to about 55 weight percent of the active ingredient, from about 20 weight percent to about 40 weight percent hydroxypropyl methylcellulose, from about 5 weight percent to about 15 weight percent lactose, from about 4 weight percent to about 6 weight percent microcrystalline cellulose, and from about 1 weight percent to about 5 weight percent of silicon dioxide. All of the weight percentages are based upon the total weight of the tablet dosage form.

More specifically, the controlled release tablet can be formed from a uniform admixture of about 54 weight percent of the active ingredient, about 30 weight percent hydroxypropyl methylcellulose, about 8 weight percent lactose, about 5 weight percent microcrystalline cellulose, and about 3 weight percent silicon dioxide.

More specifically, the controlled release tablet can also be formed from a uniform admixture of about 54 weight percent of the active ingredient, about 30 weight percent hydroxypropyl methylcellulose, about 8 percent lactose, about 5 weight percent microcrystalline cellulose, and about 3 weight percent silicon dioxide.

Additional substances that can be included in the above controlled release tablets, as well as methods to make the controlled release tablets, are described in U.S. Pat. No. 6,419,953.

Example 4

The active ingredient can be prepared as a controlled release gelatin capsule formed with a composite wall that contains a liquid, the active ingredient formulation, as described in U.S. Pat. No. 6,419,952; wherein the active ingredient as described herein (e.g., stearyl choline chloride) is substituted for the active ingredient described therein. The composite wall includes a barrier layer formed over the external surface of the gelatin capsule, an expandable layer formed over the barrier layer, and a semipermeable layer formed over the expandable layer.

The controlled release gelatin capsule includes a gelatin capsule containing a liquid, the active ingredient formulation; and a multilayer wall superposed on the gelatin capsule. The multilayer wall includes a deformable barrier layer, an expandable layer, a semipermeable layer; and an orifice formed or formable through the wall.

Additional substances that can be included in the above controlled release gelatin capsules, as well as methods to make the controlled release gelatin capsules, are described in U.S. Pat. No. 6,419,952.

Example 5

The active ingredient can be prepared as a sustained-release dosage form having the active ingredient surrounded by an interior and an exterior wall, with an exit that allows for administration of the active ingredient to a patient, as described in U.S. Pat. No. 6,245,357; wherein the active ingredient as described herein (e.g., stearyl choline chloride) is substituted for the active ingredient described therein.

The sustained-release dosage form can include the active ingredient, and a pharmaceutically acceptable polyethylene oxide carrier, which is coated with a wall comprising ethylcellulose and hydroxypropylcellulose.

More specifically, the sustained-release dosage form can also include the active ingredient and a pharmaceutically acceptable polyethylene oxide carrier, which is coated with an interior wall comprising ethyl cellulose and hydroxypropylcellulose, and an exterior wall containing cellulose acetate.

The sustained-release dosage form can also be prepared as a dosage form for delivering the active ingredient at a sustained-release rate to a gastrointestinal-lipid-fluid environment. The dosage form includes a composition containing a dose of the active ingredient, and a coat that envelopes the composition containing the active ingredient. The coat includes a passage-former that leaves the coat in the presence of fluid, and a wall that surrounds the coat and prevents lipid in the gastrointestinal tract from entering the dosage form.

Additional substances that can be included in the above sustained-release dosage forms, as well as methods to make the sustained-release dosage forms, are described in U.S. Pat. No. 6,245,357.

Example 6

The active ingredient can be prepared as a tablet for controlled release, as described in U.S. Pat. No. 6,033,685;

wherein the active ingredient as described herein (e.g., stearyl choline chloride) is substituted for the active ingredient described therein. The tablet includes a matrix layer having the active ingredient embedded in a non-swelling, non-gelling hydrophobic matrix; a first barrier layer laminated to a single face of the matrix layer; and an optional second barrier layer laminated to the opposite face of the matrix layer and oppositely disposed to the first barrier layer. The matrix contains up to about 80% of the active ingredient, and from about 5% to about 80% by weight of nonswellable waxes or polymeric material insoluble in aqueous medium. The first and second barrier layers independently include polymeric material exhibiting a high degree of swelling and gelling in aqueous medium, or nonswellable wax or polymeric material insoluble in aqueous medium.

Additional substances that can be included in the above controlled release tablets, as well as methods to make the controlled release tablets, are described in U.S. Pat. No. 6,033,685.

Example 7

The active ingredient can be prepared as a pharmaceutical composition for extended release of the active ingredient in a gastrointestinal environment, as described in U.S. Pat. No. 6,010,718; wherein the active ingredient as described herein (e.g., stearyl choline chloride) is substituted for the active ingredient described therein. The composition includes the active ingredient and a pharmaceutically acceptable polymer so that, when ingested orally, the composition induces statistically significantly lower $C_{max}$ in the plasma than an immediate release composition of the active ingredient. The pharmaceutical composition maintains bioavailability and minimum concentration substantially equivalent to that of an immediate release composition of the active ingredient achieved by multiple dosing.

Additional substances that can be included in the above extended release pharmaceutical compositions, as well as methods to make the extended release pharmaceutical compositions, are described in U.S. Pat. No. 6,010,718.

Example 8

The active ingredient can be prepared as orally administrable pharmaceutical preparations having controlled release of the active ingredient, as described in U.S. Pat. No. 5,900,425; wherein the active ingredient as described herein (e.g., stearyl choline chloride) is substituted for the active ingredient described therein. Such controlled release pharmaceutical preparations can include the active ingredient in amorphous form as a coprecipitate in a polyvinylpyrrolidone homo or copolymer having a weight average molecular weight of about 15,000 to 1,000,000 and, a release-delaying component containing a gel-forming polymer having a viscosity of at least 15 mPas when measured at a 2% concentration at 20° C.

Additional substances that can be included in the orally administrable extended release pharmaceutical compositions, as well as methods to make the orally administrable extended release pharmaceutical compositions are described in U.S. Pat. No. 5,900,425.

Example 9

The active ingredient can be prepared in tablet form for controlled release of the active ingredient in a dispersion as described in U.S. Pat. No. 5,882,682; wherein the active ingredient as described herein (e.g., stearyl choline chloride) is substituted for the active ingredient described therein. The tablet has a compressed core which contains the active agent, a polymer which forms gelatinous microscopic particles upon hydration, and if desired, an agent to modulate the hydration; and a water insoluble coating which adheres to and surrounds the core and contains apertures which provide an area for the hydration and release of the dispersion. The release rate of the active ingredient is a function of the number and size of the apertures in the coating of the tablet.

The active ingredient may be prepared for controlled release from a tablet as a dispersion by preparing a compressed core from an admixture containing a therapeutically effective amount of the active ingredient, a polymer which upon hydration forms gelatinous microscopic particles, and a water insoluble, water impermeable polymeric coating.

The water insoluble, water impermeable polymeric coating can contain a polymer and a plasticizer, which surrounds and adheres to the core. The polymer can include, e.g., cellulose acetate, cellulose acetate butyrate, ethylcellulose, polyvinylacetate, polyvinyl chloride, polymers of acrylic, methacrylic acid esters, or a combination thereof. The plasticizer can include, e.g., dibutylsebacate, diethylphthalate, triethylcitrate, polyethylene glycol, or a combination thereof. The polymer which upon hydration forms gelatinous microscopic particles can include, e.g., sodium polyacrylate, carboxypolymethylenes, the pharmaceutically acceptable salts thereof, or a combination thereof. The carboxypolymethylenes can be prepared from acrylic acid crosslinked with allylethers of sucrose or pentaerythritol. The coating of the tablet can have a plurality of formed apertures exposing between about 1 and about 75% of the core surface.

Additional substances that can be included in the orally administrable tablets for the controlled release of the active ingredient in a dispersion, as well as methods to make the orally administrable tablets for the controlled release of the active ingredient in a dispersion are described in U.S. Pat. No. 5,882,682.

Example 10

The active ingredient can be prepared as a tablet for controlled release of the active ingredient through use of a water-soluble alginate salt, a complex salt of alginic acid and an organic carboxylic acid in admixture with the active ingredient, as described in U.S. Pat. No. 5,705,190; wherein the active ingredient as described herein (e.g., stearyl choline chloride) is substituted for the active ingredient described therein.

A tablet for a once a day dosage of the active ingredient can be prepared that contains a therapeutically effective amount of the active ingredient, a water-soluble alginate salt, a complex salt of alginic acid, and an organic carboxylic acid. The cation of the alginic acid can be calcium, strontium, iron, or barium.

Additional substances that can be included in the orally administrable controlled release tablets, as well as methods to make the orally administrable controlled release tablets are described in U.S. Pat. No. 5,705,190.

Example 11

An oral composition of the active ingredient can be prepared for targeted slow release of the active ingredient in the intestine, as described in U.S. Pat. No. 5,643,602; wherein the active ingredient as described herein (e.g., stearyl choline chloride) is substituted for the active ingredient described therein.

Oral compositions can be prepared that contain the active ingredient in a pellet that contains a core, a layer that surrounds the core, and a membrane that surrounds the layer and the core. The core can contain the active ingredient alone or in combination with other pharmaceutically acceptable materials. The layer surrounding the core can be a pharmaceutically acceptable film-forming, water-insoluble or water-soluble polymer; a pharmaceutically acceptable mixture of film-forming, water-insoluble polymers; or a pharmaceutically acceptable mixture of film-forming, water-soluble and film-forming, water-insoluble polymers.

The membrane surrounding both the core and the layer surrounding the core can contain a pharmaceutically acceptable, film-forming, anionic carboxylic polymer that is difficult to dissolve at a low pH but that is soluble at a higher pH of about 4 to 7.5. The polymer of the membrane can be either alone or in combination with a pharmaceutically acceptable, film-forming, water-insoluble polymer. The thickness or the ratio of the anionic carboxylic polymer to the water-insoluble polymer is effective to prevent release of the active ingredient from the pellet in gastric fluids, but permits release of the active ingredient from the pellet in intestinal fluids at a rate allowing treatment of a part of the intestinal tract.

Additional substances that can be included in the orally administrable controlled release tablets that can be targeted to the intestine, as well as methods to make the orally administrable controlled release tablets that can be targeted to the intestine are described in U.S. Pat. No. 5,643,602.

Example 12

A sustained release once-a-day oral formulation of the active ingredient can be prepared that contains a therapeutically effective amount of the active ingredient and a non-aqueous semisolid matrix to impart sustained release properties to the active ingredient, as described in U.S. Pat. No. 5,433,951; wherein the active ingredient as described herein (e.g., stearyl choline chloride) is substituted for the active ingredient described therein. The non-aqueous semisolid matrix is a fatty acid glyceride and/or a polyethylene glycol ester of a fatty acid. The semisolid matrix can be a long chain fatty acid glycerides and/or one or a mixture of polyethylene glycol esters of long chain fatty acids, and mixtures thereof.

Additional substances that can be included in the orally administrable sustained release tablets, as well as methods to make the orally administrable sustained release tablets are described in U.S. Pat. No. 5,433,951.

Example 13

The active ingredient can be prepared as an orally administrable formulation that contains the active ingredient and a permeation-enhancing mixture of sodium salicylate and an oil to provide enhanced absorption of the active ingredient through the wall of the gastrointestinal tract, as described in U.S. Pat. No. 5,424,289; wherein the active ingredient as described herein (e.g., stearyl choline chloride) is substituted for the active ingredient described therein. The formulation is characterized as a solid, which provides a convenient and improved format for handling and storage and for the preparation of oral dosage forms (such as pills, capsules and delivery vessels) containing a homogeneous mixture of ingredients.

The active ingredient can be prepared as a dosage form having an orally administrable, enteric-coated capsule that contains a therapeutically effective amount of the active ingredient, 70-90 weight % of sodium salicylate, and 10-30 weight % of an oil.

Additional substances that can be included in the orally administrable tablets, as well as methods to make the orally administrable tablets are described in U.S. Pat. No. 5,424,289.

Example 14

The active ingredient can be prepared as oral controlled release dosage units that contain hydroxypropyl methylcellulose, as described in U.S. Pat. No. 5,419,918; wherein the active ingredient as described herein (e.g., stearyl choline chloride) is substituted for the active ingredient described therein. The aqueous granulation of the dosage units is performed in the presence of one or more solutes, which inhibit gel formation during granulation, but allow formation of a gel when administered orally.

Additional substances that can be included in the orally administrable dosage units, as well as methods to make the orally administrable dosage units are described in U.S. Pat. No. 5,419,918.

Example 15

The active ingredient can be prepared as a mixture of an alginate and a polyacrylate in a ratio of from 15:1 to 1:2, as described in U.S. Pat. No. 5,230,901; wherein the active ingredient as described herein (e.g., stearyl choline chloride) is substituted for the active ingredient described therein. Such mixtures are suitable for the preparation of depot drug forms.

The active ingredient may be prepared as a tablet for sustained release that includes a blend of a unit dosage of the active ingredient with a mixture of alginate and a polyacrylate in a ratio of 15:1 to 2:1. The polyacrylate can be a copolymer of neutral (meth)acrylic acid esters of methanol, ethanol and trimethylammonioethanol chloride. In addition, the ratio of the ammonium group containing ester unit to the remaining neutral (meth)acrylic acid ester units can be about 1:40.

Additional substances that can be included in the tablets, as well as methods to make the tablets, are described in U.S. Pat. No. 5,230,901.

Example 16

The active ingredient can be prepared as a controlled release pellet containing a core which includes the active ingredient, an intensive disintegrating agent, a wetting agent and a binder; and a double layer which controls release of the activate agent, as described in U.S. Pat. No. 5,204,121; wherein the active ingredient as described herein (e.g., stearyl choline chloride) is substituted for the active ingredient described therein. The double layer includes an acrylic-based outer undigestible water-permeable lacquer layer, and an inner jacket layer that contains a hydrophobic additive and hydroxypropylcellulose. The intensive disintegrating agent can be crosslinked sodium carboxymethylcellulose or sodium starch glycolate. The wetting agent can include sodium laurylsulphate. The binder can include PVP. The outer undigestible water-permeable lacquer layer can include an acrylic resin based on a poly(meth)acrylic acid ester having a neutral character or having a low content of quaternary ammonium groups. Such an acid ester can include a copoly (meth)acrylic acid ester, or an ethylcellulose. The inner jacket controls the migration of the water in the direction of the core. The inner jacket can contain hydroxypropylcellulose and a hydrophobic additive that is calcium stearate or hydrogenated castor oil.

Additional substances that can be included in the tablets, as well as methods to make the tablets, are described in U.S. Pat. No. 5,204,121.

Example 17

The active ingredient can be prepared as a sustained release formulation containing the active ingredient and a high and low viscosity HPMC, as described in U.S. Pat. No. 5,009,895; wherein the active ingredient as described herein (e.g., stearyl choline chloride) is substituted for the active ingredient described therein. The sustained release formulation will exhibit a zero order release profile.

A carrier base material can be combined with the active ingredient and shaped and compressed to a solid sustained release pharmaceutical dosage form having a zero order release profile upon administration. The carrier base material can contain a high viscosity hydroxypropylmethylcellulose (HPMC) having a molecular weight of 60,000 or greater; and a low viscosity HPMC, having a molecular weight of 50,000 or less. The high and low viscosity HPMC are in a ratio yielding a zero order release profile.

Additional substances that can be included in the sustained release formulations, as well as methods to make the sustained release formulations, are described in U.S. Pat. No. 5,009,895.

Example 18

The active ingredient can be prepared as a controlled and sustained release formulation containing a carrier base material combined with the active ingredient, as described in U.S. Pat. No. 4,983,398; wherein the active ingredient as described herein (e.g., stearyl choline chloride) is substituted for the active ingredient described therein. The carrier base material can contain a mixture of one or more nonionic cellulose ethers and an alkali metal carboxylate. At least one of the cellulose ethers can include hydroxypropylmethylcellulose having a number average molecular weight of at least 50,000.

Additional substances that can be included in the sustained release formulations, as well as methods to make the sustained release formulations, are described in U.S. Pat. No. 4,983,398.

Example 19

The active ingredient can be prepared as a controlled release formulation for the controlled release of the active ingredient, as described in U.S. Pat. No. 4,946,686; wherein the active ingredient as described herein (e.g., stearyl choline chloride) is substituted for the active ingredient described therein. The formulation includes a core composition containing a plurality of controlled release solubility modulating units that include solubility modulating agents. Each solubility modulating agent is a complexing agent or a surfactant, and is either surrounded by a water insoluble coat containing at least one pore forming additive dispersed throughout, or dispersed in an individual matrix substrate. Each unit also includes the active ingredient, and a water insoluble microporous wall that surrounds the core composition. The water insoluble microporous wall contains a polymer material that is permeable to water but substantially impermeable to solute, and at least one water leachable pore forming additive dispersed throughout the wall.

Additional substances that can be included in the controlled release formulations, as well as methods to make the controlled release formulations, are described in U.S. Pat. No. 4,946,686.

Example 20

The active ingredient can be prepared as an oral sustained release tablet having a core and a coating layer, as described in U.S. Pat. No. 4,919,938; wherein the active ingredient as described herein (e.g., stearyl choline chloride) is substituted for the active ingredient described therein. The core matrix can contain 20% to 60% w/w of a hydroxypropylmethylcellulose gelling agent, 0.41% to 20% w/w of (+)-trans-1a, 2,3,4a, 5,6-hexahydro-9-hydroxy-4-(1-propyl)-4H-naphth[1,2-b]-1,4-oxazine hydrochloride, and 2.08 to 12.5% w/w of buffering agent homogeneously dispersed therein. The core can also include suitable pharmaceutically acceptable excipients. The coating layer surrounding the core matrix can include a slowly soluble, water permeable ethyl cellulose polymer.

Additional substances that can be included in the controlled release tablets, as well as methods to make the controlled release tablets, are described in U.S. Pat. No. 4,919,938.

Example 21

The active ingredient can be prepared as a solid unit dosage form having a controlled and prolonged release pattern upon administration, as described in U.S. Pat. No. 4,849,229; wherein the active ingredient as described herein (e.g., stearyl choline chloride) is substituted for the active ingredient described therein. The dosage form can contain a mixture of a high viscosity grade methylcellulose or hydroxypropylmethylcellulose, an alkali metal sulfate or sulfonate and the active ingredient.

A therapeutically active solid unit dosage form having a controlled and prolonged release pattern upon administration, can contain a mixture of a high viscosity grade water-soluble nonionic cellulose ether having a number average molecular weight of at least 50,000 and a methoxyl content of 16.5-31.5 weight-%. The cellulose ether can include methylcellulose, hydroxypropylmethylcellulose, or mixtures thereof. The dosage form can also include an alkali metal sulfonate of aliphatic and aromatic hydrocarbons and succinic esters, and the active ingredient.

Additional substances that can be included in the dosage form, as well as methods to make the dosage form, are described in U.S. Pat. No. 4,849,229.

Example 22

The active ingredient can be prepared as a controlled, slow release, solid pharmaceutical composition that includes the active ingredient and a blend of sodium alginate and sodium-calcium alginate, as described in U.S. Pat. No. 4,842,866; wherein the active ingredient as described herein (e.g., stearyl choline chloride) is substituted for the active ingredient described therein.

Additional substances that can be included in the dosage form, as well as methods to make the dosage form, are described in U.S. Pat. No. 4,842,866.

Example 23

The active ingredient can be prepared as a controlled and prolonged release composition having a carrier base material that is combined with the active ingredient and shaped and compressed to a solid unit dosage form, as described in U.S. Pat. No. 4,795,327; wherein the active ingredient as described herein (e.g., stearyl choline chloride) is substituted for the active ingredient described therein. The carrier base material is a mixture of one or more nonionic cellulose ethers and an anionic surfactant. At least one of the cellulose ethers is methyl cellulose or hydroxypropylmethylcellulose having a number average molecular weight of at least 50,000 and a methoxyl content of 16.5-31.5 weight-%.

Additional substances that can be included in the dosage form, as well as methods to make the dosage form, are described in U.S. Pat. No. 4,795,327.

Example 24

The active ingredient can be prepared as a hydrogel reservoir containing pills that provide for controlled delivery of the active ingredient, as described in U.S. Pat. No. 4,649,043; wherein the active ingredient as described herein (e.g., stearyl choline chloride) is substituted for the active ingredient described therein. The pills include a wall surrounding a core of the active ingredient.

The hydrogel reservoir includes a matrix that contains a pharmaceutically acceptable non-toxic, non-hydrated polyethylene oxide that exhibits the ability to retain fluid within its polyethylene oxide structure, absorb fluid from the gastrointestinal tract, and expand with at least a 2 fold volume increase for retaining the hydrogel reservoir in the stomach over an extended period of time. The hydrogel reservoir includes a plurality of pills dispensed throughout the matrix of the reservoir. The pills contain a dosage amount of the active ingredient and a wall containing a release rate controlling composition that contains a cellulosic polymer that surrounds the dosage amount of the active ingredient. The matrix can contain a pharmaceutically acceptable non-toxic, non-hydrated carboxy polymer that exhibits the ability to retain fluid within its carboxy polymer structure, absorb fluid from the gastrointestinal tract, and expand with at least a 2 fold volume increase for retaining the dispensing device in the stomach over an extended period of time.

Additional substances that can be included in the hydrogel reservoirs, as well as methods to make the hydrogel reservoirs, are described in U.S. Pat. No. 4,649,043.

Example 25

The active ingredient can be prepared as a sustained release composition that is made from a plurality of pellets, as described in U.S. Pat. No. 4,634,587; wherein the active ingredient as described herein (e.g., stearyl choline chloride) is substituted for the active ingredient described therein. Each pellet can include the active ingredient-containing coating over a nonpareil seed, with a further coating of about 5 to about 15% by weight of a mixture of about 1.5 to about 9 parts by weight ethylcellulose to about 1 part by weight hydroxypropylcellulose.

Additional substances that can be included in the sustained release compositions, as well as methods to make the sustained release compositions, are described in U.S. Pat. No. 4,634,587.

Example 26

The active ingredient can be prepared as a sustained release oral formulation that contains a capsule that includes upper and lower parts that are connectible and easily separable from each other, and a plurality of micropellets present in the capsule, as described in U.S. Pat. No. 4,587,118; wherein the active ingredient as described herein (e.g., stearyl choline chloride) is substituted for the active ingredient described therein. The micropellets provide sustained release of the active ingredient when taken by a patient. The micropellets contain inner seeds coated with a mixture of theophylline and polyvinylpyrrolidone which is further coated with a mixture of ethylcellulose and hydroxypropylcellulose.

Additional substances that can be included in the sustained release compositions, as well as methods to make the sustained release compositions, are described in U.S. Pat. No. 4,587,118.

Example 27

The active ingredient can be prepared as a sustained release tablet for oral administration, as described in U.S. Pat. No. 4,556,678; wherein the active ingredient as described herein (e.g., stearyl choline chloride) is substituted for the active ingredient described therein. The tablet contains compressed granules that include the active ingredient, from about 0.1 to about 10 parts by weight hydroxypropyl methylcellulose, about one part by weight hydroxypropyl cellulose, and a lubricant. The hydroxypropyl methylcellulose will have a molecular weight of from about 20,000 to about 140,000. The hydroxypropyl cellulose will have a molecular weight of from about 60,000 to about 300,000.

Additional substances that can be included in the sustained release compositions, as well as methods to make the sustained release compositions, are described in U.S. Pat. No. 4,556,678.

Example 28

The active ingredient can be prepared as an oral unit dosage containing a carrier base material and the active ingredient for controlled and prolonged release, as described in U.S. Pat. No. 4,540,566; wherein the active ingredient as described herein (e.g., stearyl choline chloride) is substituted for the active ingredient described therein. The carrier base material can be a mixture of one or more nonionic cellulose ethers and an anionic surfactant. At least one of the cellulose ethers can be a modified hydroxypropylmethylcellulose having a number average molecular weight of less than 50,000 and has been modified by successive or concurrent exposure to moisture and air.

Additional substances that can be included in the sustained release compositions, as well as methods to make the sustained release compositions, are described in U.S. Pat. No. 4,540,566.

Example 29

The active ingredient can be prepared as a sustained release composition that contains a plurality of polymerically coated seeds of the active ingredient, as described in U.S. Pat. No. 4,508,702; wherein the active ingredient as described herein (e.g., stearyl choline chloride) is substituted for the active ingredient described therein. Each of the seeds can be individually coated with a polymeric mixture, which contains from about 1.5 to about 15 parts by weight ethylcellulose and about one part by weight hydroxypropylcellulose.

Additional substances that can be included in the sustained release compositions, as well as methods to make the sustained release compositions, are described in U.S. Pat. No. 4,508,702.

Example 30

The active ingredient can be prepared as a self-supporting polymeric diffusion matrix that provides for the sustained release of the active ingredient, as described in U.S. Pat. No. 4,482,533; wherein the active ingredient as described herein (e.g., stearyl choline chloride) is substituted for the active ingredient described therein. The matrix can contain from about 1 to about 60% by weight of a polar plasticizer; from about 5 to about 20% by weight polyvinylalcohol having a molecular weight from about 50,000 to about 150,000; from about 10 to about 25% by weight polyvinylalcohol having a molecular weight from about 4,000 to about 15,000; from about 2 to about 30% by weight polyvinylpyrrolidone; a pharmaceutically effective amount of the active ingredient to provide a sustained release of the active ingredient over a prolonged period; and from about 5 to about 20% by weight of diethanol myristoylamide. The diethanol myristoylamide can function to bring the components into solution.

Additional substances that can be included in the sustained release matrixes, as well as methods to make the sustained release matrixes, are described in U.S. Pat. No. 4,482,533.

Example 31

The active ingredient can be prepared as a sustained release oral dosage form as a tablet having a core that contains a pharmaceutically effective amount of the active ingredient, as described in U.S. Pat. No. 4,432,965; wherein the active ingredient as described herein (e.g., stearyl choline chloride) is substituted for the active ingredient described therein. The tablet core can be coated with a sustained release polymeric coating which contains about 5 to about 20 percent by weight polyethylene glycol component having a molecular weight of from about 500 to about 2000, and from about 80 to 95 percent by weight polyvinylalcohol component. The polyvinylalcohol component can contain from about one to about ten parts by weight of a partially hydrolyzed polyvinylalcohol subcomponent having a molecular weight of from about 50,000 to about 110,000 and having a degree of hydrolysis of from about 75 to about 92 percent. The polyvinylalcohol component can also contain about one part by weight of a substantially completely hydrolyzed polyvinylalcohol subcomponent having a molecular weight of from about 90,000 to about 150,000 and having a degree of hydrolysis in excess of 95%.

Additional substances that can be included in the sustained release oral dosage forms, as well as methods to make the sustained release oral dosage forms, are described in U.S. Pat. No. 4,432,965.

Example 32

The active ingredient can be prepared as pharmaceutical tablets, lozenges, suppositories and other solid dosage unit forms that have a prolonged and regular release pattern of the active ingredient, as described in U.S. Pat. No. 4,226,849; wherein the active ingredient as described herein (e.g., stearyl choline chloride) is substituted for the active ingredient described therein. The shaped dosage unit can contain a carrier base material of hydroxypropylmethylcellulose or a mixture thereof with up to 30% ethylcellulose and/or up to 30% sodium carboxymethylcellulose. The carrier base material can be subjected to hydrolysis and oxidation, so as to generate a desired minimum concentration of carbonyl and carboxyl groups, and then admixed and shaped with the active ingredient of the invention.

Additional substances that can be included in the sustained release dosage forms, as well as methods to make the sustained release dosage forms, are described in U.S. Pat. No. 4,226,849.

Example 33

The active ingredient can be prepared as a sustained release composition that utilizes a pellet formulation encapsulated in a hard gelatin capsule, as described in U.S. Pat. No. 4,173,626; wherein the active ingredient as described herein (e.g., stearyl choline chloride) is substituted for the active ingredient described therein. A portion of the pellets can be uncoated for immediate and rapid release of the active ingredient for elevating the plasma level of the active ingredient. The remainder of the pellets can be coated with a polymer to sustain the plasma level of the active ingredient. The uncoated and coated pellets may be mixed with non-medicated pellets as a capsule filler.

Additional substances that can be included in the sustained release compositions, as well as methods to make the sustained release compositions, are described in U.S. Pat. No. 4,173,626.

Example 34

The active ingredient can be prepared as a controlled release solid dosage composition, as described in U.S. Pat. No. 6,365,196; wherein the active ingredient as described herein (e.g., stearyl choline chloride) is substituted for the active ingredient described therein. The composition can include a dissolution rate stabilizer and a hydrophobic waxy material. The composition can contain about 40 to 90% by weight of the active ingredient, a hydrophobic waxy material in about 5 to 30% by weight, a dissolution rate stabilizer in an amount greater than 1% to about 15% by weight; and optional pharmaceutically acceptable excipients.

Additional substances that can be included in the above compositions, as well as methods to make the compositions are described in U.S. Pat. No. 6,365,196.

Example 35

The active ingredient can be prepared as a stabilized solid controlled release dosage form, as described in U.S. Pat. No. 6,316,031; wherein the active ingredient as described herein (e.g., stearyl choline chloride) is substituted for the active ingredient described therein. The controlled release dosage form can have an inert bead coated with the active ingredient, a barrier layer over the bead that is coated with the active ingredient, and a controlled release layer that is added over the barrier layer.

The barrier layer can include hydroxypropylmethylcellulose. The barrier layer can be coated with a controlled release layer derived from an aqueous dispersion of plasticized ethylcellulose in an amount sufficient to obtain controlled release of the active ingredient when the bead is exposed to a gastrointestinal fluid. The coated bead will be cured at a temperature greater than the glass transition temperature of the plasticized ethylcellulose for at least about 24 hours. This will cause individual ethylcellulose particles in the coating to coalesce and to gradually slow the release of the active ingredient when the bead is exposed to aqueous fluid until an endpoint is reached. When the endpoint is reached, the active ingredient will be released in amounts which do not significantly vary at any time point along the dissolution curve by more than about 20% of the total amount of the active ingredient released, when compared to the in-vitro dissolution of the coated bead prior to curing.

Additional substances that can be included in the above compositions, as well as methods to make the compositions are described in U.S. Pat. No. 6,316,031.

Example 36

The active ingredient can be prepared as a stable solid controlled release composition, as described in U.S. Pat. No. 6,143,353; wherein the active ingredient as described herein (e.g., stearyl choline chloride) is substituted for the active ingredient described therein. The stable solid controlled release composition will have a coating derived from an aqueous dispersion of a hydrophobic acrylic polymer that includes a substrate containing the active ingredient that is overcoated with an aqueous dispersion of a plasticized water-insoluble acrylic polymer. The composition will provide stable dissolution of the active ingredient that is unchanged after exposure to accelerated storage conditions.

The plasticized water-insoluble acrylic polymer contains monomers that can be, for example, an ester of acrylic acid, an ester of methacrylic acid, an alkyl ester of acrylic acid, an alkyl ester of methacrylic acid, and mixtures of any of the foregoing. The compositions can include an additional material that is a polymerizable permeability-enhancing agent, a water-soluble acrylic polymer, a pore-former, and mixtures of any of the foregoing. This will provide controlled release of the active ingredient when the coated substrate is exposed to an environmental fluid.

Additional substances that can be included in the above compositions, as well as methods to make the compositions are described in U.S. Pat. No. 6,143,353.

Example 37

The active ingredient can be prepared as a controlled release composition having microparticles that contain the active ingredient in a polymeric matrix, as described in U.S. Pat. No. 5,688,530; wherein the active ingredient as described herein (e.g., stearyl choline chloride) is substituted for the active ingredient described therein.

The polymeric matrix is a biodegradable, biocompatible polymeric matrix of a 40/60 to 60/40 polylactide-co-glycolide ester of a polyol. The polyol is a ($C_{3-6}$) carbon chain containing alcohol having 3 to 6 hydroxyl groups, or a monosaccharide and a disaccharide. The esterified polyol will have at least 3 polylactide-co-glycolide chains.

Additional substances that can be included in the above compositions, as well as methods to make the compositions are described in U.S. Pat. No. 5,688,530.

Example 38

The active ingredient can be prepared as a capsule containing a plurality of coated particles that contain a therapeutically effective amount of the active ingredient, as described in U.S. Pat. No. 5,656,291; wherein the active ingredient as described herein (e.g., stearyl choline chloride) is substituted for the active ingredient described therein.

The particles are coated with a barrier membrane providing a controlled, preferably pH-independent, release of the active ingredient. The particles will contain at least one water insoluble component (e.g. ethyl cellulose, copolymers of acrylic and methacrylic esters, or natural or synthetic waxes). The water insoluble component will provide a pH-independent drug release.

Additional substances that can be included in the above compositions, as well as methods to make the compositions are described in U.S. Pat. No. 5,656,291.

Example 39

The active ingredient can be prepared as a multilayered controlled release pharmaceutical dosage composition, as described in U.S. Pat. No. 5,645,858; wherein the active ingredient as described herein (e.g., stearyl choline chloride) is substituted for the active ingredient described therein.

The multilayered controlled release pharmaceutical dosage composition contains a plurality of coated particles. Each particle contains a core that will contain the active ingredient and a mixture of hydroxypropyl methylcellulose, polyethylene glycol and propylene glycol. The core will be overcoated with a controlled release barrier layer that will contain ethyl cellulose. The controlled release barrier that coats the core will be overcoated with another layer that contains the active ingredient and a mixture of hydroxypropyl methylcellulose, polyethylene glycol and propylene glycol. The second layer that contains the active ingredient will be overcoated with another controlled release barrier layer that will contain ethyl cellulose.

Additional substances that can be included in the above compositions, as well as methods to make the compositions are described in U.S. Pat. No. 5,645,858.

Example 40

The active ingredient can be prepared as a sustained release homogeneous tablet or homogeneous tablet layer, as described in U.S. Pat. No. 5,462,747; wherein the active ingredient as described herein (e.g., stearyl choline chloride) is substituted for the active ingredient described therein.

The table or tablet layer can be formed by making a wet granulation using povidone (PVP) in alcohol as the granulating fluid. The wet granulation can then be dried, milled, and blended with a dry powdered erosion promotor, wicking agent, lubricant, and a glidant. The mixture can be compressed to produce a tablet or tablet coating which, upon administration to a patient, results in a long-lasting slow and relatively regular incremental release of the active ingredient. The mixture can be used to produce multilayer tablets for immediate release and sustained release of the active ingredient. An example of a wicking agent is microcrystalline cellulose. An example of an erosion promoter is pregelatinized starch. An example of a lubricant is magnesium stearate. An example of a glidant is silicon dioxide.

Additional substances that can be included in the above compositions, as well as methods to make the compositions are described in U.S. Pat. No. 5,462,747.

Example 41

The active ingredient can be prepared as a sustained release homogeneous tablet or homogeneous tablet layer, as described in U.S. Pat. No. 5,393,765; wherein the active ingredient as described herein (e.g., stearyl choline chloride) is substituted for the active ingredient described therein.

The active ingredient of the invention can be prepared as an erodible pharmaceutical composition providing a unique zero order controlled release profile. The erodible composition can contain between about 5% to about 60% w/w of the active ingredient which has a solubility of less than about 80 mg/mL. The composition can also contain about 5% to about 50% w/w of hydroxypropyl methylcellulose having a viscosity from about 50 to about 100 centipoises. The remainder of the composition will consist of inert carriers.

Additional substances that can be included in the above compositions, as well as methods to make the compositions are described in U.S. Pat. No. 5,393,765.

Example 42

The active ingredient can be prepared as a composition for the sustained release of the active ingredient, as described in U.S. Pat. No. 5,356,635; wherein the active ingredient as described herein (e.g., stearyl choline chloride) is substituted for the active ingredient described therein.

The composition includes an amorphous carbohydrate glass matrix containing a suitable carbohydrate and the active ingredient which retards the recrystallization of the carbohydrate and the active ingredient. The matrix will also have a water-insoluble wax dispersed throughout the matrix.

Additional substances that can be included in the above compositions, as well as methods to make the compositions are described in U.S. Pat. No. 5,356,635.

Example 43

The active ingredient can be prepared as a composition for the sustained release of the active ingredient, as described in U.S. Pat. No. 5,328,697; wherein the active ingredient as described herein (e.g., stearyl choline chloride) is substituted for the active ingredient described therein.

The composition will have the active ingredient layered onto non-pareil seeds which are sprayed with a glycine solution. Next, a coating of a wax mixture is applied.

Additional substances that can be included in the above compositions, as well as methods to make the compositions are described in U.S. Pat. No. 5,328,697.

Example 44

The active ingredient can be prepared as a stable sustained release the active ingredient-resin composition for use in liquid carrier for oral administration, as described in U.S. Pat. No. 5,186,930; wherein the active ingredient as described herein (e.g., stearyl choline chloride) is substituted for the active ingredient described therein.

The composition contains the active ingredient-resin particle that is coated with a first inner coating of a high temperature melting water-insoluble pharmaceutically acceptable wax and a second outer coating of a pharmaceutically acceptable water-insoluble polymer. The active ingredient-resin particle contains the active ingredient ionically bonded to a pharmaceutically acceptable ion exchange resin particle. The amount of the first inner coating is sufficient to prevent the resin in the active agent-resin particle from swelling and cracking the second outer coating. The active ingredient is released when the complex is placed in a liquid carrier.

Additional substances that can be included in the above compositions, as well as methods to make the compositions are described in U.S. Pat. No. 5,186,930.

Example 45

The active ingredient can be prepared as a stable sustained release the active ingredient-resin composition for use in a liquid carrier for oral administration, as described in U.S. Pat. No. 4,892,742; wherein the active ingredient as described herein (e.g., stearyl choline chloride) is substituted for the active ingredient described therein.

The controlled release composition in table form contains a core element that includes about 65-95% by weight of a water soluble the active ingredient, 5-35% by weight of a water insoluble polymeric matrix; and a membrane coating comprising 5-10% by weight of the tablet. The membrane contains a rate-controlling polymer. The insoluble polymeric matrix can contain ethyl cellulose or zein. The insoluble polymer matrix can also contain an oil or wax-like material (e.g. stearic acid, stearyl alcohol, cetyl alcohol, fatty acids, long chain fatty alcohols, carnuba wax, beeswax, white wax, vegetable oil and fatty acid glycerides of $C_{6-18}$ fatty acids). The membrane coating can be cellulose (e.g. ethyl cellulose, mixtures of ethyl cellulose and hydroxypropyl methylcellulose or hydroxypropyl cellulose). The membrane coating can further contain a plasticizer (e.g. triacetin, propylene glycol, polyethylene glycol having a molecular weight of 200 to 800, dibutyl phthalate, dibutyl sebacate, fatty acid, vegetable oils and glycerides of $C_{6-18}$ fatty acids).

Additional substances that can be included in the above compositions, as well as methods to make the compositions are described in U.S. Pat. No. 4,892,742.

Example 46

The active ingredient can be prepared as a stable sustained release dosage composition for use in a liquid carrier for oral administration, as described in U.S. Pat. No. 4,781,919; wherein the active ingredient as described herein (e.g., stearyl choline chloride) is substituted for the active ingredient described therein.

The dosage compositions are made of saponified starch-acrylonitrile graft copolymers and the active ingredient. The sustained release injectable dosage forms can contain an effective amount of the active ingredient, and an effective amount of a water insoluble, water swellable, saponified starch acrylonitrile graft copolymer to provide sustained release of the active ingredient upon injection into a patient in need of such treatment.

Additional substances that can be included in the above compositions, as well as methods to make the compositions are described in U.S. Pat. No. 4,781,919.

Example 47

The active ingredient can be prepared as a controlled release dosage composition containing the active ingredient in combination with hydroxypropylmethylcellulose USP 2910, as described in U.S. Pat. No. 4,695,591; wherein the active ingredient as described herein (e.g., stearyl choline chloride) is substituted for the active ingredient described therein.

The hydroxypropylmethylcellulose USP 2910 can be less than about one-third of the total dosage form weight of hydroxypropylmethylcellulose USP 2910.

Additional substances that can be included in the above compositions, as well as methods to make the compositions are described in U.S. Pat. No. 4,695,591.

Example 48

The active ingredient can be prepared as a controlled release dosage composition containing an plurality of micronized pellets, as described in U.S. Pat. No. 4,524,060; wherein the active ingredient as described herein (e.g., stearyl choline chloride) is substituted for the active ingredient described therein.

The micronized pellets will contain the active ingredient, a water-channelling agent, a wetting agent, and a disintegrant. The mixture can be in the form of a non-compressed pellet having an enteric coat or a sustained release coat permeable to gastrointestinal juices. The micronized pellets can be placed into sustained-release capsules.

Additional substances that can be included in the above compositions, as well as methods to make the compositions are described in U.S. Pat. No. 4,524,060.

Additional formulations that can be prepared to include the active ingredient, and methods of preparing the formulations are described, e.g., in U.S. Pat. Nos. 6,419,953; 6,251,432; 6,197,344; 6,150,410; 6,033,685; 6,010,718; 5,705,190; 5,268,182; 5,169,642; 6,419,952; 6,395,292; 6,375,978; 6,368,626; 6,342,249; 6,245,357; 6,174,547; 6,077,538; 5,650,170; 5,540,912; 5,512,293; 4,871,548; 4,740,198; 4,692,144; 6,270,799; 5,900,425; 5,707,655; 5,204,121; 5,368,862; 5,366,738; 5,009,895; 4,983,400; 4,919,938; 4,900,755; 4,832,957; 4,639,458; 4,173,626; 5,690,960; 5,660,837; 5,419,918; 4,863,743; 4,634,587; 4,587,118; 4,556,678; 4,508,702; 4,432,965; 4,428,926; 4,428,925; 6,500,454; 6,495,162; 6,492,488; 6,437,000; 6,426,091; 6,419,958; 6,419,953; 6,419,952; 6,416,786; 6,403,120; 6,387,404; 6,372,252; 6,337,091; 6,303,144; 6,284,275; 6,274,171; 6,261,601; 6,254,891; 6,221,395; 6,210,714; 6,197,339; 6,162,466; 6,162,463; 6,156,343; 6,150,410; 6,149,940; 6,136,343; 6,126,967; 6,106,863; 6,099,862; 6,099,859; 6,093,387; 6,090,411; 6,083,533; 6,074,669; 6,056,977; 6,046,177; 6,033,686; 6,033,685; 6,030,642; 6,030,641; 6,027,748; 6,024,982; 5,980,942; 5,945,125; 5,885,615; 5,879,707; 5,874,107; 5,869,100; 5,849,330; 5,846,563; 5,783,212; 5,776,489; 5,736,159; 5,681,583; 5,681,582; 5,667,801; 5,656,291; 5,654,005; 5,645,848; 5,626,874; 5,624,683; 5,614,218; 5,603,956; 5,601,842; 5,593,694; 5,582,837; 5,578,321; 5,576,021; 5,562,915; 5,558,879; 5,554,387; 5,543,155; 5,512,297; 5,508,041; 5,505,962; 5,500,227; 5,498,422; 5,492,700; 5,484,607; 5,466,460; 5,462,747; 5,455,046; 5,433,951; 5,427,799; 5,427,798; 5,407,686; 5,397,574; 5,368,862; 5,362,424; 5,358,723; 5,334,393; 5,334,392; 5,292,534; 5,292,533; 5,283,065; 5,277,912; 5,219,572; 5,200,193; 5,164,193; 5,162,117; 5,126,145; 5,091,189; 5,085,865; 5,075,114; 5,073,380; 5,055,306; 5,051,261; 5,019,398; 5,015,479; 5,007,790; 5,004,613; 5,002,774; 4,983,401; 4,968,509; 4,966,768; 4,933,185; 4,925,676; 4,892,742; 4,882,167; 4,861,590; 4,837,032; 4,824,678; 4,822,619; 4,820,522; 4,816,262; 4,806,359; 4,803,079; 4,803,076; 4,800,083; 4,798,725; 4,795,645; 4,795,642; 4,792,448; 4,784,858; 4,775,535; 4,756,911; 4,734,285; 4,710,384; 4,708,834; 4,695,467; 4,692,337; 4,690,824; 4,666,705; 4,629,620; 4,629,619; 4,610,870; 4,587,118; 4,571,333; 4,557,925; 4,556,678; 4,520,009; 4,505,890; 4,503,031; 4,432,965; 4,415,547; 4,353,887; 4,322,311; 4,308,251; 4,264,573; 4,252,786; 4,173,626; 4,138,475; 4,122,157; 4,002,458; and 3,977,992.

Alternatively, the active ingredient can be administered in a formulation that will form a biodegradable or bioerodible implant, either ex vivo or in vivo. The biodegradable or bioerodible implant, upon degrading in vivo, will release the active ingredient over a suitable period of time. Such formulations that will form a biodegradable implant, either ex vivo or in vivo, are described, e.g., in U.S. Pat. Nos. RE37,950; 6,461,631; 6,395,293; 6,261,583; 6,180,129; 6,143,314; 6,120,789; 6,113,938; 6,071,530; 5,990,194; 5,945,115; 5,888,533; 5,861,166; 5,780,044; 5,759,563; 5,744,153; 5,739,176; 5,736,152; 5,733,950; 5,702,716; RE35,601; 5,630,808; 5,599,552; 5,487,897; 5,413,572; 5,368,859; 5,340,849; 5,324,519; 5,320,616; 5,278,202; 5,278,201; 5,238,687; 5,234,693; 5,234,692; 5,137,727; 5,112,614; 5,057,318; 4,996,060; 4,455,144; 4,367,741; 4,346,709; 4,340,054; 4,304,232; 4,249,531; 4,142,526; 4,093,709; 4,069,307; and 3,948,254.

The following prophetic examples can be performed:

Example 49

Test of Stearyl Choline Chloride (PP-100) in Scopolamine Impaired Rats

This study will evaluate a proprietary choline derivative (PP-100), in comparison to a marketed cholinesterase inhibiting compound (donepezil), for its ability to improve (1) spatial learning and memory formation and (2) recall of learned spatial information, in scopolamine impaired Long-Evans rats. The behavioral assessment will be performed by NeuroDetective Inc. ("NDI"), dba NeuroDetective International.

This study will be conducted in the laboratory of Dr. Alvin V. Terry at the University of Georgia College of Pharmacy, CJ-1020, Medical College of Georgia, Augusta, Ga., 30912-2450, under the supervision of NDI. Five groups (n=10/group) of 3-4 month-old male Long Evans rats will each receive one daily dose (p.o.) of either of two doses of the choline derivative, donepezil HCL, or vehicle, beginning ten days prior to initiation of behavior testing. Daily dosing then continues throughout the five days of behavior testing (see below).

Fifty male 3-4 month old Long Evans rats (Harlan) will be housed and tested in the Small Animal Behavior Core facility located at the Medical College of Georgia, Augusta, Ga., USA. Administrative responsibility for this facility is assigned to the Office of Laboratory Animal Services, Medical College of Georgia. The facility is accredited by the Association for Assessment and Accreditation of Laboratory Animal Care International (AAALAC), and is a Registered Research Facility with the United States Department of Agriculture (USDA No. 57-R-0002), and has an Office of Laboratory Animal Welfare OLAW Assurance Statement (A2207-01, dated Apr. 3, 2000 and on file).

Test subjects will be housed doubly in polycarbonate cages with Bed-O-Cob® bedding in a temperature-controlled room (25° C.) with a 12 hr light/dark cycle. Upon arrival, animals will be provided with water and food (Teklad Rodent Feed® or Purina Rat Chow®) ad libitum. All rats will be handled daily for a minimum of one week prior to behavioral testing. All procedures employed during this study have been reviewed and approved by the Medical College of Georgia Committee on Animal Use for Research (CAURE) and are consistent with AAALAC guidelines.

All animals in the experimental groups will be weighed prior to the experiment and the dosing volume will be based on the animals' individual body weights. Animals will be observed for clinical signs after each dose administration.

Test articles will be prepared according to the supplied instructions. The animals will be dosed via oral gavage (p.o.) once daily for 10 days prior to initiation of the Morris water maze task (described below), once daily during the 4 days of water maze testing, and once on the following day prior to the probe trial (described below). In addition, thirty minutes prior to the first trial of the water maze, 0.1-0.5 mg/kg of scopolamine will be administered IP to four of the five groups (those receiving subsequent injections of test drugs or saline vehicle). The fifth group will serve as a non-scopolamine control. The specific dosage of scopolamine will be determined prior to initiation of water maze testing. Fifteen minutes after the scopolamine administration, the four groups of rats will be dosed with one of the following: 40 mg/kg or 10× the scopolamine dosage of PP-100, 0.75 mg/kg of donepezil, or an equivalent volume of 0.9% saline at the same times as the other groups are administered scopolamine and test drug.

Test article solutions of the appropriate concentration are made in saline. Test article solutions will be aliquoted each day and stored in a −18° C. freezer, then discarded after 30 days. On the day of dosing one portion of each dose strength will be removed, thawed and brought to room temperature prior to dosing. The intended vehicle is 0.9% saline, however if PP-100 at the proscribed dosages proves insoluble in saline or does not appear to suspend well, 2.5% methylcellulose will be used as vehicle.

In order to test effects of the compounds on both acquisition and recall of spatial memories, the visible platform task and the hidden platform task will be utilized. The rationale for using these tests is based on published studies demonstrating that the experimental paradigm of finding a platform hidden beneath the water surface in a swimming pool reveals spatial learning and memory capabilities of the rodent (e.g., Stewart and Morris, In: *The water maze*, A. Sahgal (ed.), Vol. 1, Oxford University Press, pp. 107-122 (1993); Sutherland et al., *J. Neuro.*, 8:1863 (1988)). Scopolamine is known to impair performance in the water maze task, and blockage of scopolamine effects is known to reduce impairment in the water maze (e.g., Gattu et al., *Pharma. Biochem. Behav.*, 4:793 (1997)).

Testing Apparatus.

To determine the effects of the test agents on spatial learning, water maze experiments will be performed in a circular pool (diameter: 180 cm, height: 76 cm) made of black plastic. The pool will be filled to a depth of 35 cm of water (maintained at 25.0±1.0° C.) and located in a large room with a number of extra-maze visual cues including geometric images (squares, triangles, circles etc.) hung on the wall, diffuse lighting, and black curtains used to hide the experimenter (visually) and the resting test subjects. Swimming activity of each rat will be monitored via a television camera mounted overhead, which relays information including latency to find the platform, total distance traveled, time and distance spent in each quadrant etc. to a video tracking system (Actimetrics, Evanston, Ill.). Tracking is adjusted to accommodate white rats on a black background.

Visible Platform Task.

On the day prior to initiation of water maze testing, a visible platform test will be performed as a general estimate of visual acuity. In this pre-test, a highly visible (white) cover fitted with a small white flag is attached to a small, black 10 cm square platform, which raises the surface of the platform approximately 1.0 cm above the surface of the water. This platform is placed in the center of the SW quadrant of the pool. Each rat is given one or more trials with a 90 sec time limit to locate this platform. This is accomplished by lowering the rat into the water, first in the NE quadrant, and then allowing the rat to locate and climb onto the platform. When the rat is successful (on its own accord without assistance) it is then given a series of 4 additional trials (with a 1.0 min intertrial interval) and the latency (in sec) to locate the platform is recorded. The platform is moved on each trial to a different quadrant and the animal is always entered from the opposite quadrant until the test is conducted once in all 4 quadrants. Animals that are unable to locate the platform within the 90 sec cutoff period for more than 2 of the 4 trials (after the initial successful trial) are removed from the study.

Hidden Platform Task.

Following the visible platform test, the platform is submerged approximately 1.0 cm below the surface of the water and placed in the center of the NE quadrant. Each rat is given 4 trials per day for 4 consecutive days to locate and climb onto the hidden platform. A trial is initiated by placing the rat in the water facing the pool wall one of the 4 quadrants. The daily order of entry into individual quadrants is pseudo-randomized such that all 4 quadrants are used every day. For each trial, the rat is allowed to swim a maximum of 90 sec, in order to find the platform. When successful the rat is allowed a 30-sec rest period on the platform. If unsuccessful within the allotted time period, the rat is given a score of 90 sec and then physically placed on the platform and also allowed the 30-sec rest period. In either case the rat is given the next trial after an additional 1.5 min rest period (i.e., ITI=2.0 min).

Probe Trial (Transfer Test).

On the day following the last trial of the hidden platform task, a single probe trial is conducted, in which the platform is removed from the pool to measure memory for the previous platform location. The animal is placed in the pool and time and distance traveled each of the 4 quadrants plus the number of crossings over the previous platform location, are recorded.

Measurement and Analysis of Performance.

Analysis of performance utilizes image analysis software (Water Maze Video Tracking System, Actimetrics Software Evanston, Ill.). Latency (time) to reach the platform and swim path length are recorded during the water maze test, while total time in each quadrant and swim path length in each quadrant are recorded in the probe trial, along with number of crossings of the previous location of the hidden platform.

Evaluation of Test Results.

All statistical analyses will be conducted without knowledge of group identity. Latencies, swim path lengths, and time spent in the different quadrants of the pool (Probe Trial) as well as platform crossings (probe trial) and swim speeds will be compared across groups using repeated measures ANOVA, with post-hoc comparisons made using Fischer's PLSD test at a significance level of $p<0.05$. In the probe trial percent time spent in the target quadrant and in the opposite quadrant will also be compared across groups. Average swim speeds for each test will be compared across groups using a randomized block ANOVA, with post hoc comparisons made using Fischer's PLSD test at a significance level of $p<0.05$.

Example 50

Comparison of Stearyl Choline Chloride (PP-100) and Donepezil HCl (Aricept®) in Scopolamine Impaired Rats Purpose This example compared two doses of the choline analog PP-100 with the currently marketed, best selling Alzheimer's disease therapeutic agent, donepezil HCl (Aricept®*), for effects on learning and memory using a scopolamine-induced cognitive impairment model in rats.

Design

Male Long-Evans rats (3 months of age) were administered either saline, donepezil (0.75 mg/kg), or PP-100 (3.0 mg/kg or 40.0 mg/kg) by oral gavage for 10 days prior to (and during the 5 days of) testing in a water maze task. The compounds were evaluated for their ability to reverse the amnestic effects of scopolamine (0.1 mg/kg) in this task.

Results

Donepezil (0.75 mg/kg) and PP-100 (40 mg/kg) both appeared to reverse the effects of scopolamine in the later 2 days of hidden platform testing. PP-100 (40 mg/kg) treated animals also learned faster and more efficiently than donepezil treated animals during the middle portion of learning.

There were no treatment effects in the probe trials, which primarily assay memory, most likely because of the high (near maximum) level at which the animals learned this task by the fourth day of hidden platform testing.

The particular dose of scopolamine used tended to produce impairment in the animals' learning to swim to a visible platform. This effect was exacerbated by, and reached statistical significance when combined with, both doses of PP-100. This impairment may be indicative of altered visual acuity in these animals.

Notwithstanding the potential confounding effect described above, all treatment groups did learn the hidden platform task and performed the task quite efficiently by the fourth day of testing.

Methods

Fifty male 3-month-old Long Evans rats (Harlan Sprague-Dawley, Inc.) were housed and tested in the Small Animal Behavior Core facility located at the Medical College of Georgia, Augusta, Ga., USA and directed by Dr. Alvin V. Terry Jr. General animal care and administrative responsibility for this facility is assigned to the Office of Laboratory Animal Services, Medical College of Georgia. The facility is accredited by the Association for Assessment and Accreditation of Laboratory Animal Care International (AAALAC), is a Registered Research Facility with the United States Department of Agriculture (USDA No. 57-R-0002), and has an Office of Laboratory Animal Welfare OLAW Assurance Statement (A2207-01; dated Apr. 3, 2000) on file.

Test subjects were housed in pairs in polycarbonate cages with Bed-O-Cob® bedding in a temperature-controlled room (25° C.) with a 12 hr light/dark cycle. Upon arrival, animals were provided with water and food (Teklad Rodent Feed® or Purina Rat Chow®) ad libitum. All rats were handled daily for a minimum of one week prior to behavioral testing. The procedures employed during this study were reviewed and approved by the Medical College of Georgia Committee on Animal Use for Research (CAURE) and are consistent with AAALAC guidelines. The subjects used in the experimental groups were weighed prior to the experiment and the dose volume was based on the animals' individual body weights. Animals were observed for visible signs of adverse effects after each dose administration.

Drug Administration

The animals were randomly assigned to one of 5 groups (n=10/group) and administered one daily dose of either of two doses of the choline derivative PP-100 (3 or 40 mg/kg), donepezil HCL (0.75 mg/kg), or vehicle (0.9% saline), via oral gavage (p.o.) beginning ten days prior to initiation of the water maze task. Daily dosing continued through the initial day of visible platform testing and the subsequent five days of water maze testing (i.e., on hidden platform test days as well as probe trial days). On both the single day of pre-testing (Visible Platform Test) as well as on each day of watermaze testing, thirty minutes prior to the first trial, 0.1 mg/kg of scopolamine hydrobromide was administered i.p. to four of the five groups (i.e., excluding the saline-saline group). Fifteen minutes after the scopolamine injection (or vehicle) each group was dosed with one of the test articles or vehicle (see Table 1 for an overview of the testing protocol). Test articles were prepared according to the supplied instructions, and aliquots of the solutions were stored (at −20° C.). Test agents were freshly thawed at the time of use.

Procedures

In order to test and compare the effects of PP-100 on both acquisition and recall of spatial memories, the water maze hidden platform task was utilized. The rationale for using this test is based on published studies demonstrating that the experimental paradigm of finding a platform hidden beneath the water surface in a swimming pool reveals spatial learning and memory capabilities of the rodent (e.g., Stewart and Morris, In: *The water maze* A. Sahgal (ed.), Vol. 1, Oxford University Press, pp. 107-122 (1993); Sutherland et al., *J. Neuro.*, 8:1863 (1988)). Scopolamine is known to impair performance in the water maze task, and blockage of scopolamine effects is known to reduce impairment in the water maze (e.g., Terry et al., *Drug Dev. Res.*, 47:97 (1999)).

Testing Apparatus

The water maze experiment was performed in a circular pool (diameter=180 cm, height=76 cm) made of black plastic. The pool was filled with water to a depth of 35 cm and the water was maintained at 25.0±1.0° C. The pool was located in a large room with a number of extra-maze visual cues including geometric images (squares, triangles, circles etc.) hung on the wall, diffuse lighting, and black curtains used to hide the experimenter (visually) and the resting test subjects. Swimming activity of each rat was monitored via a television camera mounted overhead, which relayed information including latency to find the platform, total distance traveled, time and distance spent in each quadrant etc. to a video tracking system (Actimetrics, Evanston, Ill.).

Visible Platform Task

On the day prior to initiation of water maze testing, a visible platform test was performed as a general estimate of visual acuity. In this pre-test, a highly visible (white) cover fitted with a small white flag was attached to a small, square platform submerged beneath the surface of the water (described below), which effectively raised the surface of the platform to approximately 1.0 cm above the surface of the water. Each rat was given one or more trials with a 90 sec time limit to locate the platform visually. This was accomplished by lowering the rat into the water in the NE quadrant and allowing the rat to locate and climb onto the platform, which was located in center of the opposite quadrant of the pool. When the rat was successful (on its own accord, i.e. without experimenter assistance) it was then given a series of 4 additional trials (with a 1.0 min inter-trial interval) and the latency (in sec) to locate the platform was recorded. On each of these trials the platform was moved to the center of a different quadrant and the animal was always placed into the pool from the opposite quadrant until the test was conducted once in all 4 quadrants.

Hidden Platform Task

For the water maze test itself, the escape platform was submerged. The platform was an invisible (black) 10 cm square, submerged approximately 1.0 cm below the surface of the water and placed in the center of the NE quadrant. Each rat was given 4 trials per day for 4 consecutive days to locate and climb onto the hidden platform. A trial was initiated by placing the rat in the water facing the pool wall in one of the 4 quadrants. The daily order of entry into individual quadrants was pseudo-randomized such that all 4 quadrants were used every day. For each trial, the rat was allowed to swim a maximum of 90 sec, in order to find the platform. When successful the rat was allowed a 30-sec rest period on the platform. If unsuccessful within the allotted time period, the rat was given a score of 90 sec and then physically placed on the platform and also allowed the 30-sec rest period. In either case the rat was given the next trial after an additional 1.5 min rest period (i.e., total inter-trial interval=2.0 min).

Probe Trial (Transfer Test)

On the day following the last trial of the hidden platform task, a single probe trial was conducted, in which the platform was removed from the pool to measure memory for the previous platform location. The animal was placed in the pool and time and distance traveled in each of the 4 quadrants plus the number of crossings over the previous platform location, were recorded.

Measurement and Analysis of Performance

All data were collated and entered into Microsoft Excel spreadsheets, and subsequently imported into SigmaStat version 2.03 for statistical analyses. Statistical analyses were conducted without knowledge of group identity. Latencies, swim path lengths, swim speeds, and time spent in the previous target quadrant of the pool (Probe Trial) as well as the number of crossings of the previous platform location were compared across groups using Repeated Measures ANOVA, with post-hoc comparisons made using Fischer's PLSD test at a significance level of $p<0.05$.

In many cases the data sets did not meet the criteria for either normality or equal variance (or both), and so the data were first either transformed or ranked and then analyzed by ANOVA. All figures show the untransformed data, while statements of statistical significance are based on the transformed or ranked data (when performed). It should be noted that in the analysis of the data from the Visible Platform Test, no data transformation resulted in normality; statistical analysis used least-squares transformed data.

Results

Visible Platform Test

FIG. 1 illustrates a trend toward impairment in locating a highly visible platform in the watermaze pre-test, for all treated groups compared to untreated (Saline-Saline). In the overall ANOVA (2-way repeated measures), this trend produced a significant Group effect, $F_{4,45}=3.0$, $p<0.03$. Performance improved over the 4 trials, as indicated by a significant Trial effect, $F_{3,12}=5.3$, $p<0.01$. There was no significant Group×Trial interaction. In post-hoc Fischer's tests, the impairment in locating the visible platform was statistically significant in all trials for animals receiving PP-100 at the lower dose, and in the latter two trials for animals receiving PP-100 at the higher dose.

Hidden Platform Test

Figure 2:
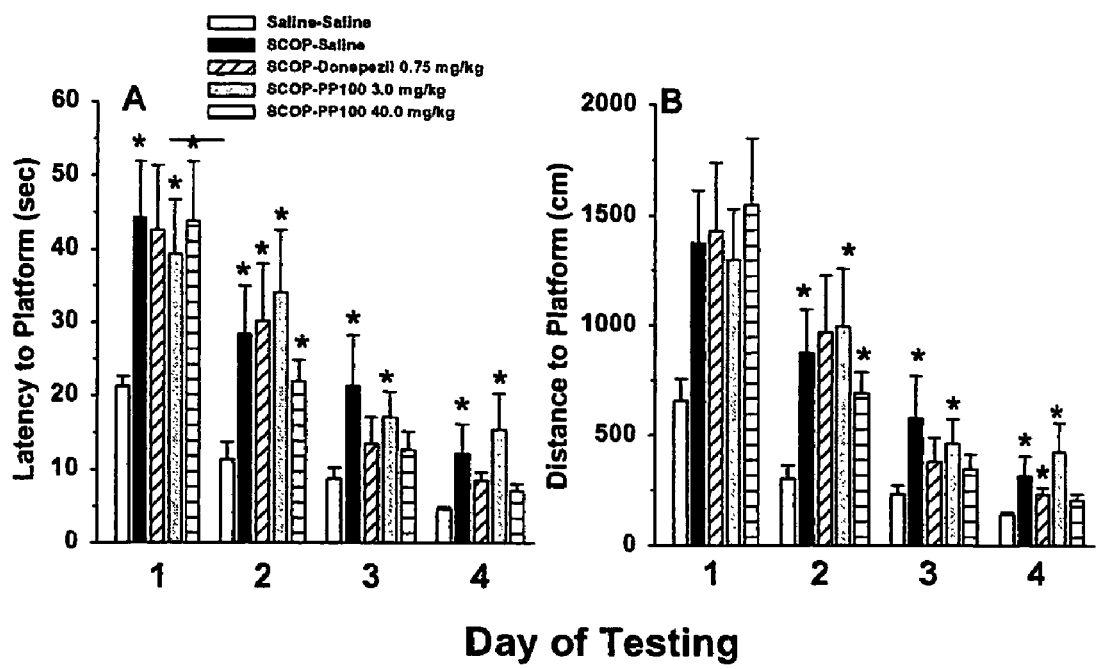
FIG. 2. (A) Mean latency in seconds (±s.e.m.) and (B) distance traveled in cm (±s.e.m.) to locate a hidden platform by the various groups in the watermaze learning task over 4 trials. *=$p<0.05$ vs. Saline-Saline by post-hoc Fischer's LSD test following significant overall two-way repeated measures ANOVA. N=10 rats per group.
Figure 3:
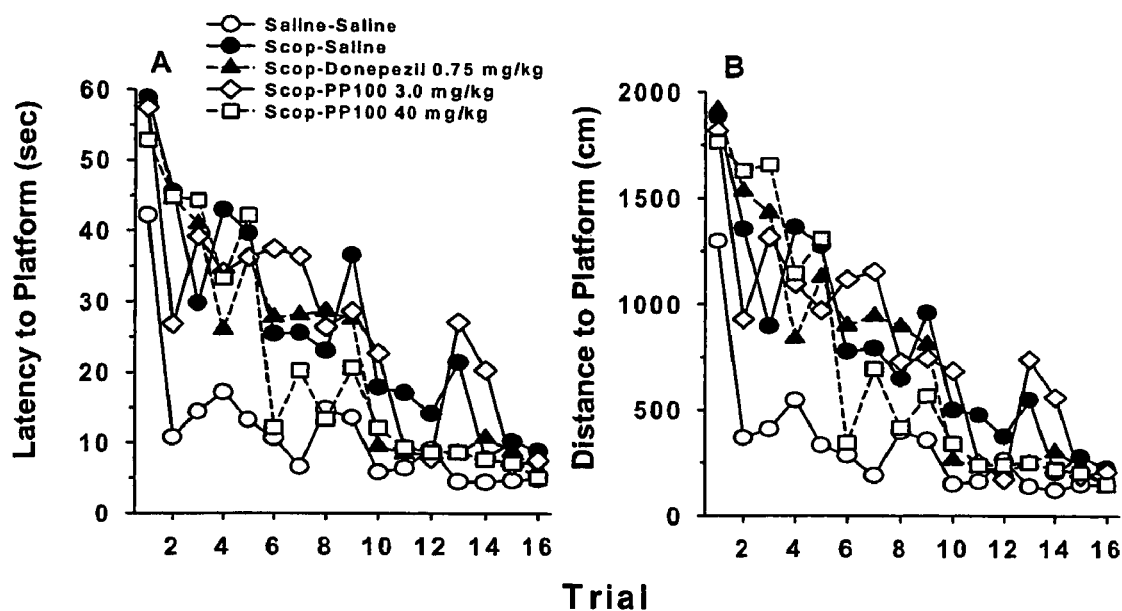
FIG. 3. (A) Mean latency in seconds (±s.e.m.) and (B) distance traveled in cm (±s.e.m.) to locate a hidden platform by the various groups in the watermaze learning task over 16 individual trials. There was a consistent trend of faster latencies and shorter swim distances in reaching the hidden platform by the PP-100 at 40 mg/kg group. However, this effect did not achieve statistical significance. N=10 rats per group.

As expected in this task, there was a significant improvement in performance over testing days, as indicated by a significant Day effect in both the latency ($F_{3,12}=77.4$, $p<0.001$) and swim distance measures ($F_{3,12}=65.5$, $p<0.001$). Also as expected, scopolamine impaired learning, as indicated by the overall Group effect ($F_{4,45}=4.8$, $p<0.01$ in the latency measure, $F_{4,45}=4.4$, $p<0.01$ in the swim distance measure). As illustrated in FIG. 2, post-hoc Fischer's tests indicated that on test days 1 and 2 animals administered scopolamine generally performed less efficiently than saline controls whether or not donepezil or the PP-100 compounds were administered. On days 3 and 4, however, performance of animals administered donepezil or PP100 at 40 mg/kg (in combination with scopolamine) did not differ (statistically) from saline controls indicating at least a partial reversal of the scopolamine effect later in learning. This was true for both endpoint measures, latency to find the platform and swim path length. There was also a consistent trend of faster latencies and shorter swim distances in reaching the hidden platform by animals receiving PP 100 at 40 mg/kg, compared to animals receiving donepezil, from trials #6 through #9, although this effect never achieved statistical significance (FIG. 3).

Swim Speeds

There were no treatment effects on swim speed ($F_{4,45}=2.0$, $p=0.10$). All groups tended to swim more rapidly on earlier than later days (overall Day effect, $F_{3,12}=26.4$, $p<0.001$), with no significant Treatment x Day interaction ($F_{35,199}=1.5$, $p=0.10$).

Probe Trial

Figure 4:
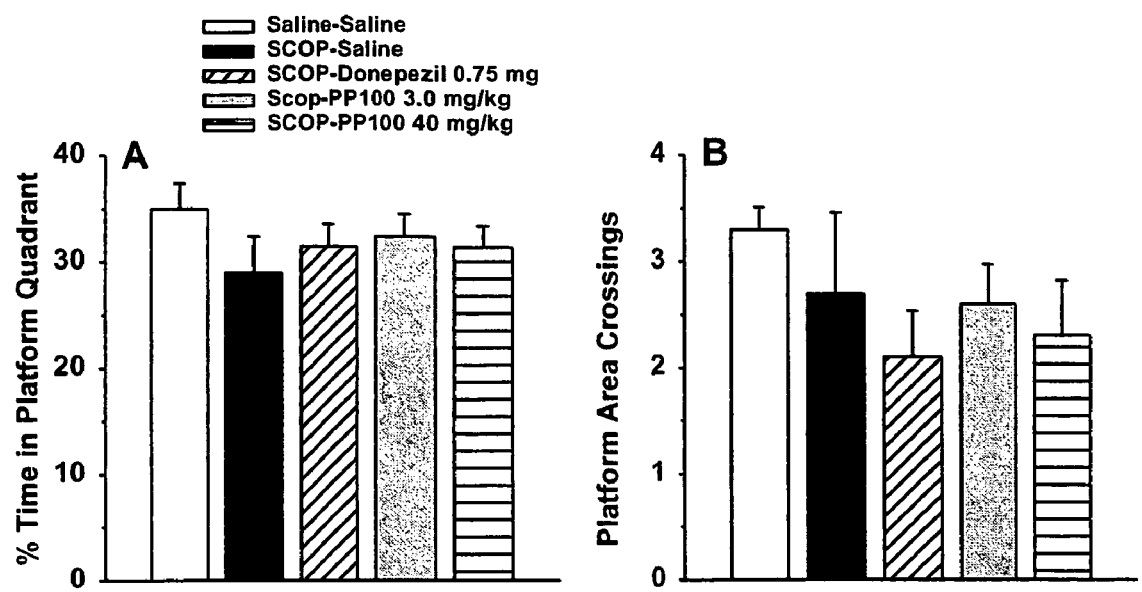
FIG. 4. Performance of probe trials by the various groups. Each bar represents the mean (±s.e.m.) of (A) percentage of time spent in the quadrant that previously contained the hidden platform; and (B) the mean number of crossings over the area (10 sq. cm) of the previous location of the hidden platform. N=10 rats per group.

FIG. 4 illustrates the performance of the different groups in the probe trial. There were no significant effects of drug treatment on the animals' memory for the prior platform location, as measured by either percentage of time spent in the quadrant of the previous platform location ($F_{4,45}=0.7$, $p=0.60$), or the mean number of crossings over the previous platform area ($F_{4,45}=0.9$, $p=0.50$).

Summary and Conclusions:

Donepezil (0.75 mg/kg) and PP-100 (40 mg/kg) appeared to at least partially reverse the effects of scopolamine in the latter 2 days of hidden platform testing. PP-100 (40 mg) treated animals also tended to learn the spatial location of the hidden platform faster and more efficiently (shorter swim path length) than donepezil treated animals (trials#6-9).

There were no treatment effects observed in the probe trials, as indicated by percent time spent in the previous target quadrant and the number of crossings over the previous platform area. This is most likely due to the high (near maximum) level of learning the hidden platform task, as noted above.

The dose of scopolamine used in this study with Long Evans rats led to some impairment in the animals' ability to locate a highly visible platform, possibly indicative of adverse effects on visual acuity. This effect was exacerbated by PP-100.

Notwithstanding the possible effect on visual acuity, all scopolamine groups did learn the hidden platform task and performed quite efficiently by the fourth day of testing.

TABLE 1

| | Testing Protocol | | |
|---|---|---|---|
| | | August 3 through August 8 | |
| Group | July 25 through August 7 (Oral Gavage) | 30 minutes before testing (IP dosing) | 15 Minutes Before Testing (Oral Gavage) |
| 1 | Vehicle | Vehicle | Vehicle |
| 2 | Vehicle | Scopolamine 0.1 mg/kg | Vehicle |
| 3 | Donepezil 0.75 mg/kg | Scopolamine 0.1 mg/kg | Donepezil 0.75 mg/kg |

TABLE 1-continued

Testing Protocol

| Group | July 25 through August 7 (Oral Gavage) | August 3 through August 8 | |
|---|---|---|---|
| | | 30 minutes before testing (IP dosing) | 15 Minutes Before Testing (Oral Gavage) |
| 4 | PP-100 3.0 mg/kg | Scopolamine 0.1 mg/kg | PP-100 3.0 mg/kg |
| 5 | PPI-100 40 mg/kg | Scopolamine 0.1 mg/kg | PPI-100 40 mg/kg |

Example 51

Evaluating the Acute Oral Toxicity of PP-100

The acute toxicity of PP-100, following oral administration of a single dose to CD-1 mice, was evaluated. The mice were observed for 14 days, clinical signs and bodyweights were recorded, necropsy was performed on all the mice, and the maximum non-lethal dose was determined.

Methods

Animals

A total of 32 CD-1 mice Crl: CD-1 (ICR) IGS (16 males and 16 females) were used. The mice weighed approximately 16-25 g and were approximately 9-14 weeks old on arrival. The mice were bred and supplied by Harlan Interfauna Ibérica, S. L. (Ctra. Sant Miquel del Fai, km 3, Apartado 38, 08182-Sant Feliu de Codines, Barcelona, Spain). On arrival, mice were housed in Makrolon cages (46.5×22.0×14.5 cm) with sawdust bedding. The mice underwent a preliminary observation and acclimatisation period of one week. The mice used in the initial study weighed 24-28 g on administration. The mice used in the follow-up study weighed 25-30 g (males) and 25-28 g (females) on administration.

The mice were individually marked with an identification code using an ear-punch technique and were housed in Makrolon cages (46.5×22.0×14.5 cm) with sawdust bedding. Each cage contained up to five mice during the preliminary observation and acclimatisation period. The cages of each group were placed on racks to avoid the effect of any external factors, such as environmental conditions, on the mice. The temperature in the animal house ranged approximately from 19 to 21° C. during the experimental period. The relative humidity was 40-70%. Artificial lighting was controlled to give 12 hours of light (7:00 am to 7:00 pm) and 12 hours of darkness.

The mice were allowed free access to a standard rat diet SAFE A04C (Scientific Animal Food & Engineering, 91360-Villemoisson sur Orge, France) which had been analysed by the manufacturer. Water was also freely available in bottles for all the mice. The water, supplied by Compañia de Aguas de Sabadell, S. A., was periodically checked for contaminants.

Administration

PP-100 was supplied by Hass-Pharma and was stored at 20±5° C. in a desiccator. PP-100 was mortared, dissolved in physiological saline (0.9% NaCl), and kept in an ultrasound bath for 2-5 minutes. PP-100 was administered orally by gastric gavage using a graduated syringe with a metal cannula. PP-100 was administered once, at a volume of 20 mL/kg, for each administered dose. The administration volume for each mouse was calculated taking into account body weight at the time of administration.

In an initial study, each dosage of PP-100 was administered to groups of mice of two males and two females each. The dosages administered were 3000 mg/kg, 4000 mg/kg and 5000 mg/kg. In a follow-up study, each dosage of PP-100 was administered to groups of mice of five males and five females each. The dosages administered were 4000 mg/kg and 5000 mg/kg.

In the initial study, after the administration the mice were observed at least twice daily over 14 days. The observations included, but were not limited to, changes in skin or fur, eyes and mucous membranes, respiratory, circulatory, central nervous and autonomic nervous systems, somatomotor activity and behaviour.

In the follow-up study, the mice were observed frequently on the day of administration to record clinical signs. In addition, the mice were also observed at least twice daily during the 14-day observation period or until death. The observations included, but were not limited to, changes in skin or fur, eyes and mucous membranes, respiratory, circulatory, central nervous and autonomic nervous systems, somatomotor activity and behaviour. At the end of this observation period, the surviving mice were sacrificed and underwent the terminal procedures described hereinbelow. The mouse that died in the course of the study underwent the same terminal procedures.

At the end of the observation period, all the surviving mice were sacrificed by intraperitoneal injection of sodium pentobarbital, and necropsies were performed on all the mice from the follow-up study. The necropsy included an examination of the intact mouse and all its superficial tissues, followed by an observation of the cranial, thoracic and abdominal cavities. All mice were weighed before administration, halfway through the observation period, and again at death.

Results

Initial Study

One male administered 5000 mg/kg PP-100 died within 24 hours of administration. No mortality was recorded in the mice treated with 4000 or 3000 mg/kg.

On the day of drug administration, abnormal gait was recorded in one female treated with 5000 mg/kg and in a male administered a dose of 3000 mg/kg, beginning 2-3 hours after treatment. Some mice treated at doses of 5000, 4000 and 3000 mg/kg showed hunched back and abnormal gait between the first and ninth day of the observation period.

Likewise, piloerection was recorded between the first and third day of the observation period in one female administered 5000 mg/kg, in two females treated with 4000 mg/kg, and in one male administered 3000 mg/kg. One female administered at the dose of 4000 mg/kg and one male treated at 3000 mg/kg had palpebral ptosis during the day following administration. Between the third and eighth day of the observation period, one female administered 3000 mg/kg had difficulties standing on her right hind limb.

Follow-Up Study

Table 2 shows the mortality data obtained for the doses of 5000 and 4000 mg/kg during the observation period. The death of one male treated with 5000 mg/kg was recorded during the first day of the observation period.

TABLE 2

| Dose level mg/kg | Animal number | Day of treatment | 1 | 2 | 3 | 4 | 5 | 6 | 7 | 8 | 9 | 10 | 11 | 12 | 13 | 14 | Total |
|---|---|---|---|---|---|---|---|---|---|---|---|---|---|---|---|---|---|
| | | | \multicolumn{17}{c}{Number of deaths during observation period} | | | | | | | | | | | | | | | | | |
| \multicolumn{18}{c}{MORTALITY OF MALE: MAIN STUDY} | | | | | | | | | | | | | | | | | | |
| 5000 | 5 | 0 | 1 | 0 | 0 | 0 | 0 | 0 | 0 | 0 | 0 | 0 | 0 | 0 | 0 | 0 | 1 |
| 4000 | 5 | 0 | 0 | 0 | 0 | 0 | 0 | 0 | 0 | 0 | 0 | 0 | 0 | 0 | 0 | 0 | 0 |
| \multicolumn{18}{c}{MORTALITY OF FEMALE: MAIN STUDY} | | | | | | | | | | | | | | | | | | |
| 5000 | 5 | 0 | 0 | 0 | 0 | 0 | 0 | 0 | 0 | 0 | 0 | 0 | 0 | 0 | 0 | 0 | 0 |
| 4000 | 5 | 0 | 0 | 0 | 0 | 0 | 0 | 0 | 0 | 0 | 0 | 0 | 0 | 0 | 0 | 0 | 0 |

Tables 3 and 4 show the clinical signs recorded for the mice treated at the dose of 5000 mg/kg on the day of administration and during the 14 days of observation, for males and females, respectively. Tables 5 and 6 show the clinical signs recorded for the mice treated at the dose of 4000 mg/kg on the day of administration and during the 14 days of observation, for males and females, respectively. These are expressed as the number of affected mice.

TABLE 3

CLINICAL OBSERVATIONS
Expressed as the number of animals affected

| OBSERVATION PERIOD (DAYS) Time following administration | \multicolumn{8}{c}{Day of treatment} | | | | | | | | | \multicolumn{14}{c}{Days after treatment} | | | | | | | | | | | | | |
|---|---|---|---|---|---|---|---|---|---|---|---|---|---|---|---|---|---|---|---|---|---|---|
| | \multicolumn{6}{c}{minutes} | | | | | \multicolumn{2}{c}{hours} | | | | | | | | | | | | |
| | 0-5 | 6-15 | 16-30 | 31-60 | 61-90 | 91-120 | 2-3 | 3-4 | 1 | 2 | 3 | 4 | 5 | 6 | 7 | 8 | 9 | 10 | 11 | 12 | 13 | 14 |
| No. of surviving animals | 5 | 5 | 5 | 5 | 5 | 5 | 5 | 5 | 5 | 4 | 4 | 4 | 4 | 4 | 4 | 4 | 4 | 4 | 4 | 4 | 4 | 4 |
| No anomalies detected | 5 | 5 | 5 | 5 | 5 | 3 | 3 | 2 | | | | | | 3 | 3 | 3 | 3 | 3 | 3 | 4 | 4 | 4 |
| Irritable | | | | | | | | | | | | | | | | | | | | | | |
| Lethargic | | | | | | | | | | | | | | | | | | | | | | |
| Unconscious | | | | | | | | | | | | | | | | | | | | | | |
| Increased motor activity | | | | | | | | | | | | | | | | | | | | | | |
| Decreased motor activity | | | | | | | | | | | | | | | | | | | | | | |
| Abnormal gait | | | | | | | | 2 | 5 | 4 | 4 | 4 | 3 | 1 | | | | | | | | |
| Decreased muscle tone | | | | | | | | | | | | | | | | | | | | | | |
| Prostration | | | | | | | | | | | | | | | | | | | | | | |
| Hunched back | | | | | | 2 | 2 | 2 | 3 | 3 | 1 | | | | | | | | | | | |
| Opisthotonos | | | | | | | | | | | | | | | | | | | | | | |
| Tremors | | | | | | | | | | | | | | | | | | | | | | |
| Clonic convulsions | | | | | | | | | | | | | | | | | | | | | | |
| Tonic convulsions | | | | | | | | | | | | | | | | | | | | | | |
| Apnoea | | | | | | | | | | | | | | | | | | | | | | |
| Brachypnoea | | | | | | | | | | | | | | | | | | | | | | |
| Tachypnoea | | | | | | | | | | | | | | | | | | | | | | |
| Dyspnoea | | | | | | | | | | | | | | | | | | | | | | |
| Cyanosis | | | | | | | | | | | | | | | | | | | | | | |
| Pallor | | | | | | | | | | | | | | | | | | | | | | |
| Rubescence | | | | | | | | | | | | | | | | | | | | | | |
| Piloerection | | | | | | | | | | | | | | 2 | 1 | 1 | | 1 | 1 | 1 | 1 | 1 |
| Alopecia | | | | | | | | | | | | | | | | | | | | | | |
| Salivation | | | | | | | | | | | | | | | | | | | | | | |
| Pigmented orbital secretion | | | | | | | | | | | | | | | | | | | | | | |
| Pigmented snout | | | | | | | | | | | | | | | | | | | | | | |
| Diarrhoea | | | | | | | | | | | | | | | | | | | | | | |

TABLE 3-continued

CLINICAL OBSERVATIONS
Expressed as the number of animals affected

| OBSERVATION PERIOD (DAYS) | Day of treatment | | | | | | | | Days after treatment | | | | | | | | | | | | | |
|---|---|---|---|---|---|---|---|---|---|---|---|---|---|---|---|---|---|---|---|---|---|---|
| Time following | minutes | | | | | | hours | | | | | | | | | | | | | | | |
| administration | 0-5 | 6-15 | 16-30 | 31-60 | 61-90 | 91-120 | 2-3 | 3-4 | 1 | 2 | 3 | 4 | 5 | 6 | 7 | 8 | 9 | 10 | 11 | 12 | 13 | 14 |
| Palpebral ptosis | | | | | | | | | 1 | | | | | | | | | | | | | |
| Right eye closed. Eyelids adhered | | | | | | | | | 1 | | | | | | | | | | | | | |
| Swollen abdomen | | | | | | | | | 5 | 4 | 4 | 4 | 1 | 1 | 1 | | | | | | | |

TABLE 4

CLINICAL OBSERVATIONS
Expressed as the number of animals affected

| OBSERVATION PERIOD (DAYS) | Day of treatment | | | | | | | | Days after treatment | | | | | | | | | | | | | |
|---|---|---|---|---|---|---|---|---|---|---|---|---|---|---|---|---|---|---|---|---|---|---|
| Time following | minutes | | | | | | hours | | | | | | | | | | | | | | | |
| administration | 0-5 | 6-15 | 16-30 | 31-60 | 61-90 | 91-120 | 2-3 | 3-4 | 1 | 2 | 3 | 4 | 5 | 6 | 7 | 8 | 9 | 10 | 11 | 12 | 13 | 14 |
| No. of surviving animals | 5 | 5 | 5 | 5 | 5 | 5 | 5 | 5 | 5 | 5 | 5 | 5 | 5 | 5 | 5 | 5 | 5 | 5 | 5 | 5 | 5 | 5 |
| No anomalies detected | 5 | 5 | 5 | 5 | 5 | 2 | 2 | 2 | | | | | 2 | 2 | 3 | 4 | 5 | 5 | 5 | 5 | 5 | 5 |
| Irritable | | | | | | | | | | | | | | | | | | | | | | |
| Lethargic | | | | | | | | | 1 | | | | | | | | | | | | | |
| Unconscious | | | | | | | | | | | | | | | | | | | | | | |
| Increased motor activity | | | | | | | | | | | | | | | | | | | | | | |
| Decreased motor activity | | | | | | 1 | 1 | 2 | 1 | 2 | 1 | | | | | | | | | | | |
| Abnormal gait | | | | | | | | 2 | 5 | 5 | 5 | 5 | 2 | 2 | 1 | 1 | | | | | | |
| Decreased muscle tone | | | | | | | | | | | | | | | | | | | | | | |
| Prostration | | | | | | | | | | | | | | | | | | | | | | |
| Hunched back | | | | | | 3 | 3 | 3 | 4 | 5 | 5 | 5 | 3 | 3 | 2 | 1 | | | | | | |
| Opisthotonos | | | | | | | | | | | | | | | | | | | | | | |
| Tremors | | | | | | | | | | | | | | | | | | | | | | |
| Clonic convulsions | | | | | | | | | | | | | | | | | | | | | | |
| Tonic convulsions | | | | | | | | | | | | | | | | | | | | | | |
| Apnoea | | | | | | | | | | | | | | | | | | | | | | |
| Brachypnoea | | | | | | | | | | | | | | | | | | | | | | |
| Tachypnoea | | | | | | | | | | | | | | | | | | | | | | |
| Dyspnoea | | | | | | | | | | | | | | | | | | | | | | |
| Cyanosis | | | | | | | | | | | | | | | | | | | | | | |
| Pallor | | | | | | | | | | | 1 | | | | | | | | | | | |
| Rubescence | | | | | | | | | | | | | | | | | | | | | | |
| Piloerection | | | | | | 3 | 3 | 3 | 5 | 5 | 2 | | 1 | 1 | 1 | 1 | | | | | | |
| Alopecia | | | | | | | | | | | | | | | | | | | | | | |
| Salivation | | | | | | | | | | | | | | | | | | | | | | |
| Pigmented orbital secretion | | | | | | | | | | | | | | | | | | | | | | |
| Pigmented snout | | | | | | | | | | | | | | | | | | | | | | |
| Diarrhoea | | | | | | | | | | | | | | | | | | | | | | |
| Palpebral ptosis | | | | | | | | | 2 | 2 | | | | | | | | | | | | |

TABLE 4-continued

CLINICAL OBSERVATIONS
Expressed as the number of animals affected

| OBSERVATION PERIOD (DAYS) | Day of treatment | | | | | | | | Days after treatment | | | | | | | | | | | | |
|---|---|---|---|---|---|---|---|---|---|---|---|---|---|---|---|---|---|---|---|---|---|
| Time following | minutes | | | | | | hours | | Days after treatment | | | | | | | | | | | | |
| administration | 0-5 | 6-15 | 16-30 | 31-60 | 61-90 | 91-120 | 2-3 | 3-4 | 1 | 2 | 3 | 4 | 5 | 6 | 7 | 8 | 9 | 10 | 11 | 12 | 13 | 14 |
| Swollen abdomen | | | | | | | | | 1 | 3 | 5 | 3 | | | | | | | | | | |
| Dark faeces | | | | | | | | | | 1 | | | | | | | | | | | | |

TABLE 5

CLINICAL OBSERVATION
Expressed as the number of animals affected

| OBSERVATION PERIOD (DAYS) | Day of treatment | | | | | | | | Days after treatment | | | | | | | | | | | | |
|---|---|---|---|---|---|---|---|---|---|---|---|---|---|---|---|---|---|---|---|---|---|
| Time following | minutes | | | | | | hours | | Days after treatment | | | | | | | | | | | | |
| administration | 0-5 | 6-15 | 16-30 | 31-60 | 61-90 | 91-120 | 2-3 | 3-4 | 1 | 2 | 3 | 4 | 5 | 6 | 7 | 8 | 9 | 10 | 11 | 12 | 13 | 14 |
| No. of surviving animals | 5 | 5 | 5 | 5 | 5 | 5 | 5 | 5 | 5 | 5 | 5 | 5 | 5 | 5 | 5 | 5 | 5 | 5 | 5 | 5 | 5 | 5 |
| No anomalies detected | 5 | 5 | 5 | 5 | 4 | 4 | 4 | 4 | 5 | 5 | 5 | 5 | 5 | 5 | 5 | 5 | 5 | 5 | 5 | 5 | 5 | 5 |
| Irritable | | | | | | | | | | | | | | | | | | | | | | |
| Lethargic | | | | | | | | | | | | | | | | | | | | | | |
| Unconscious | | | | | | | | | | | | | | | | | | | | | | |
| Increased motor activity | | | | | | | | | | | | | | | | | | | | | | |
| Decreased motor activity | | | | | | | | | | | | | | | | | | | | | | |
| Abnormal gait | | | | | 1 | 1 | 1 | 1 | | | | | | | | | | | | | | |
| Decreased muscle tone | | | | | | | | | | | | | | | | | | | | | | |
| Prostration | | | | | | | | | | | | | | | | | | | | | | |
| Hunched back | | | | | 1 | 1 | 1 | 1 | | | | | | | | | | | | | | |
| Opisthotonos | | | | | | | | | | | | | | | | | | | | | | |
| Tremors | | | | | | | | | | | | | | | | | | | | | | |
| Clonic convulsions | | | | | | | | | | | | | | | | | | | | | | |
| Tonic convulsions | | | | | | | | | | | | | | | | | | | | | | |
| Apnoea | | | | | | | | | | | | | | | | | | | | | | |
| Brachypnoea | | | | | | | | | | | | | | | | | | | | | | |
| Tachypnoea | | | | | | | | | | | | | | | | | | | | | | |
| Dyspnoea | | | | | | | | | | | | | | | | | | | | | | |
| Cyanosis | | | | | | | | | | | | | | | | | | | | | | |
| Pallor | | | | | | | | | | | | | | | | | | | | | | |
| Rubescence | | | | | | | | | | | | | | | | | | | | | | |
| Piloerection | | | | | | | | | | | | | | | | | | | | | | |
| Alopecia | | | | | | | | | | | | | | | | | | | | | | |
| Salivation | | | | | | | | | | | | | | | | | | | | | | |
| Pigmented orbital secretion | | | | | | | | | | | | | | | | | | | | | | |
| Pigmented snout | | | | | | | | | | | | | | | | | | | | | | |
| Diarrhoea | | | | | | | | | | | | | | | | | | | | | | |
| Palpebral ptosis | | | | | | | | | | | | | | | | | | | | | | |

TABLE 6

CLINICAL OBSERVATIONS
Expressed as the number of animals affected

| OBSERVATION PERIOD (DAYS) | Day of treatment | | | | | | | | Days after treatment | | | | | | | | | | | | | |
|---|---|---|---|---|---|---|---|---|---|---|---|---|---|---|---|---|---|---|---|---|---|---|
| Time following | minutes | | | | | | hours | | | | | | | | | | | | | | | |
| administration | 0-5 | 6-15 | 16-30 | 31-60 | 61-90 | 91-120 | 2-3 | 3-4 | 1 | 2 | 3 | 4 | 5 | 6 | 7 | 8 | 9 | 10 | 11 | 12 | 13 | 14 |
| No. of surviving animals | 5 | 5 | 5 | 5 | 5 | 5 | 5 | 5 | 5 | 5 | 5 | 5 | 5 | 5 | 5 | 5 | 5 | 5 | 5 | 5 | 5 | 5 |
| No anomalies detected | 5 | 4 | 4 | 5 | 3 | 3 | 2 | 4 | 5 | 5 | 5 | 5 | 5 | 5 | 5 | 5 | 5 | 5 | 5 | 5 | 5 | 5 |
| Irritable | | | | | | | | | | | | | | | | | | | | | | |
| Lethargic | | | | | | | | | | | | | | | | | | | | | | |
| Unconscious | | | | | | | | | | | | | | | | | | | | | | |
| Increased motor activity | | | | | | | | | | | | | | | | | | | | | | |
| Decreased motor activity | | | | | | | | | | | | | | | | | | | | | | |
| Abnormal gait | | | | | 2 | 2 | 3 | | | | | | | | | | | | | | | |
| Decreased muscle tone | | | | | | | | | | | | | | | | | | | | | | |
| Prostration | | | | | | | | | | | | | | | | | | | | | | |
| Hunched back | | | | | 1 | 1 | 1 | | | | | | | | | | | | | | | |
| Opisthotonos | | | | | | | | | | | | | | | | | | | | | | |
| Tremors | | | | | | | | | | | | | | | | | | | | | | |
| Clonic convulsions | | | | | | | | | | | | | | | | | | | | | | |
| Tonic convulsions | | | | | | | | | | | | | | | | | | | | | | |
| Apnoea | | | | | | | | | | | | | | | | | | | | | | |
| Brachypnoea | | | | | | | | | | | | | | | | | | | | | | |
| Tachypnoea | | | | | | | | | | | | | | | | | | | | | | |
| Dyspnoea | | | | | | | | | | | | | | | | | | | | | | |
| Cyanosis | | | | | | | | | | | | | | | | | | | | | | |
| Pallor | | | | | | | | | | | | | | | | | | | | | | |
| Rubescence | | | | | | | | | | | | | | | | | | | | | | |
| Piloerection | | 1 | 1 | | 1 | | | 1 | | | | | | | | | | | | | | |
| Alopecia | | | | | | | | | | | | | | | | | | | | | | |
| Salivation | | | | | | | | | | | | | | | | | | | | | | |
| Pigmented orbital secretion | | | | | | | | | | | | | | | | | | | | | | |
| Pigmented snout | | | | | | | | | | | | | | | | | | | | | | |
| Diarrhoea | | | | | | | | | | | | | | | | | | | | | | |
| Palpebral ptosis | | 1 | | | | | | | | | | | | | | | | | | | | |

On the day of administration, hunched back was observed in two males and three females treated with 5000 mg/kg starting 90-120 minutes after treatment. Two of these females and two males administered the same dose showed abnormal gait starting 3-4 hours after administration.

In three females and one male administered 4000 mg/kg abnormal gait was recorded, as well as hunched back in the male and in one of the females, starting 60-90 minutes after treatment. In three females receiving 4000 mg/kg, piloerection was observed between 5-15 minutes and 3-4 hours following treatment, and palpebral ptosis in one of them for 5-15 minutes following drug administration.

During the days following treatment, all the mice administered the 5000 mg/kg dose showed signs of abnormal gait between the first and eighth day of the observation period. Hunched back, piloerection and swollen abdomens were observed in the majority of mice treated with this dose between the first and eleventh day of the observation period. Two females treated with 5000 mg/kg showed reduced motor activity and palpebral ptosis between the first and third day of the observation period. In one of them irritability was also noted on the day after treatment, along with pallor and dark coloured feces on the second day of the observation period.

The male administered 5000 mg/kg, which died on the first day of the observation period, showed signs of abnormal gait, hunched back, piloerection, palpebral ptosis and swollen abdomen before death. The mouse's right eye was also closed and appeared to have adhered eyelids.

No clinical signs were recorded in the mice treated with 4000 mg/kg during the days following the administration.

The body-weight gain of the mice is shown in Tables 7 and 8. The mean body-weight gain was normal in the males treated with 5000 mg/kg and in the mice treated with 4000 mg/kg. In two of the females administered 5000 mg/kg weight loss of 3 and 1 grams respectively was recorded during the seven days following administration, however later recuperation of this weight was observed.

TABLE 7

BODY WEIGHT OF MALE MICE (g): MAIN STUDY

| Dose level (mg/kg) | Animal No. | Day of observation period |  |  | Weight at necropsy |
|---|---|---|---|---|---|
|  |  | 0 | 7 | 14 |  |
| 5000 | 31 | 26 | 29 | 33 | 33 |
|  | 32 | 30 | 34 | 36 | 36 |
|  | 33 | 25 | 28 | 32 | 32 |
|  | 34 | 29 | 33 | 36 | 36 |
|  | 35 | 26 | — | — | 22* |
|  | Mean | 27.2 | 31.0 | 34.3 | 34.3 |
|  | SD | 2.17 | 2.94 | 2.06 | 2.06 |
| 4000 | 21 | 28 | 30 | 33 | 33 |
|  | 22 | 28 | 30 | 32 | 32 |
|  | 23 | 28 | 32 | 36 | 36 |
|  | 24 | 28 | 34 | 37 | 37 |
|  | 25 | 28 | 30 | 32 | 32 |
|  | Mean | 28.0 | 31.2 | 34.0 | 34.0 |
|  | SD | 0.00 | 1.79 | 2.35 | 2.35 |

*This value is not taken into account for the calculation of the Mean and SD of the body weights in the necropsy.

TABLE 8

BODY WEIGHT OF FEMALE MICE (g): MAIN STUDY

| Dose level (mg/kg) | Animal No. | Day of observation period |  |  | Weight at necropsy |
|---|---|---|---|---|---|
|  |  | 0 | 7 | 14 |  |
| 5000 | 36 | 27 | 28 | 31 | 31 |
|  | 37 | 28 | 28 | 31 | 31 |
|  | 38 | 27 | 24 | 27 | 27 |
|  | 39 | 25 | 27 | 27 | 27 |
|  | 40 | 28 | 27 | 29 | 29 |
|  | Mean | 27.0 | 26.8 | 29.0 | 29.0 |
|  | SD | 1.22 | 1.64 | 2.00 | 2.00 |
| 4000 | 26 | 25 | 28 | 30 | 30 |
|  | 27 | 25 | 27 | 30 | 30 |
|  | 28 | 25 | 27 | 31 | 31 |
|  | 29 | 25 | 26 | 28 | 28 |
|  | 30 | 25 | 26 | 27 | 27 |
|  | Mean | 25.0 | 26.8 | 29.2 | 29.2 |
|  | SD | 0.00 | 0.84 | 1.64 | 1.64 |

During the necropsies done on all the mice of the follow-up study, a dilated small intestine containing liquid was recorded in the male treated at 5000 mg/kg which died on the first day of the observation period. No macroscopic alterations were recorded in the necropsies done on the rest of the mice treated with 5000 mg/kg, nor in the mice administered 4000 mg/kg.

The maximum non-lethal dose and the minimum lethal dose for males and females combined, and for the males separately, after 14 days of observation, were as follows: for male and female mice the maximum non-lethal dose was 4000 mg/kg and the minimum lethal dose was 5000 mg/kg; and for male mice, the maximum non-lethal dose was 4000 mg/kg, and the minimum lethal dose was 5000 mg/kg.

No mortality was recorded among the females at the tested doses. Therefore the Minimum lethal dose for the test item in females is higher than 5000 mg/kg.

Summary and Conclusions

On the first day of administration, some mice treated at doses of 5000 and 4000 mg/kg showed abnormal gait and hunched back, along with piloerection in some cases. Reduced motor activity was observed in two females at the 5000 mg/kg dose. One female treated at a dose of 4000 mg/kg had signs of palpebral ptosis about 5-15 minutes after administration.

One of the males treated at the dose of 5000 mg/kg died during the first day of the observation period. That male had a hunched back, abnormal gait, piloerection, and a swollen abdomen before death. This same mouse had its right eye closed and adhered eyelids.

During the days following administration, hunched back, abnormal gait, piloerection, and swollen abdomen were recorded in most of the mice treated at a dose of 5000 mg/kg. Likewise, two females treated at this same dose showed reduced motor activity and palpebral ptosis, along with irritability, pallor, and dark coloured feces in one particular mouse. Two of the females administered at 5000 mg/kg showed a body weight loss seven days following treatment, although a posterior recuperation in their weights was observed. Body-weight gain was normal in most of the mice administered at doses of 5000 and 4000 mg/kg.

No clinical signs were recorded among the mice treated at a dose of 4000 mg/kg during the days following administration.

During necropsies of the follow-up study, the male administered the dose of 5000 mg/kg, which died during the first day, had dilated small intestines with liquid content. No macroscopic alterations were recorded in the rest of the mice treated at doses of 5000 and 4000 mg/kg.

The maximum non-lethal dose and the minimum lethal dose for males and females combined, and for the males separately, after 14 days of observation, were as follows: for male and female mice the maximum non-lethal dose was 4000 mg/kg and the minimum lethal dose was 5000 mg/kg; and for male mice, the maximum non-lethal dose was 4000 mg/kg, and the minimum lethal dose was 5000 mg/kg. No mortality was recorded among the females at the administered doses. It was concluded that the minimum lethal dose for females is higher than 5000 mg/kg. Mortality was recorded in one male administered at the dose of 5000 mg/kg, during the first day of the observation period.

Obviously, numerous modifications and variations of the present invention are possible in light of the above teachings. It is therefore to be understood that within the scope of the appended claims, the invention may be practiced otherwise than as specifically described herein.

What is claimed is:

1. A method of treating a cognitive dysfunction that is a nonvascular dementia or a nonvascular cognitive impairment in a mammal, the method comprising administering to the mammal an effective amount of a compound of formula (I):

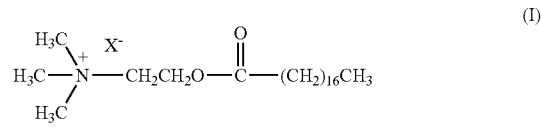

wherein,
X is a pharmaceutically acceptable counterion; or a pharmaceutically acceptable salt thereof,
wherein the nonvascular dementia or nonvascular cognitive impairment is Alzheimer's disease (AD), Huntington's disease or Parkinson's disease.

2. The method of claim 1 wherein the compound is administered in about 10 mg/day to about 10,000 mg/day.

3. The method of claim 1 wherein the compound is administered one or more times per day.

4. The method of claim 1 wherein the nonvascular dementia is dementia of the Alzheimer's type, dementia due to Parkinson's disease, or dementia due to Huntington's disease.

5. The method of claim 4 wherein the dementia of the Alzheimer's type is dementia of the Alzheimer's type without behavioral disturbance, dementia of the Alzheimer's type with behavior disturbance, dementia of the Alzheimer's type with early onset, or dementia of the Alzheimer's type with late onset.

6. A method of improving cognition functions in a mammal suffering from Alzheimer's disease type dementia, the method comprising administering to the mammal an effective amount of a compound of formula (I):

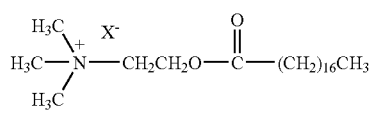

(I)

wherein,

X is a pharmaceutically acceptable counterion; or a pharmaceutically acceptable salt thereof.

7. The method of claim 1, further comprising the administration of at least one of *Ginkgo biloba, Huperzine A, Phosphatidylserine, Vitamin E, Tacrine, Donepezil, Rivastigmine, Memantine hydrochloride* (Namenda) and Galantamine.

8. The method of claim 1, wherein X is F, Cl, Br, I, sulfate, phosphate, or an organic carboxylic acid salt.

9. The method of claim 1, wherein X is Cl.

10. The method of claim 1 wherein the compound of formula (I) is:

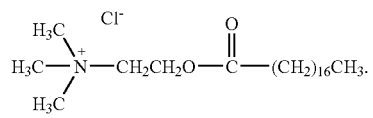

11. A method of treating, in a mammal, dementia associated with Alzheimer's disease, the method comprising administering to the mammal an effective amount of a compound of formula (I):

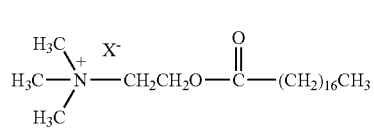

(I)

wherein,

X is a pharmaceutically acceptable counterion; or a pharmaceutically acceptable salt thereof.

12. The method of any one of claims 1, 6, and 11 wherein X is a pharmaceutically acceptable salt derived from hydrochloric acid, hydrobromic acid, sulfuric acid, sulfamic acid, phosphoric acid, or nitric acid.

13. The method of any one of claims 1, 6, and 11, wherein X is a pharmaceutically acceptable salt derived from acetic acid, propionic acid, succinic acid, glycolic acid, stearic acid, lactic acid, malic acid, tartaric acid, citric acid, ascorbic acid, pamoic acid, maleic acid, hydroxymaleic acid, phenylacetic acid, glutamic acid, benzoic acid, salicylic acid, sulfanilic acid, 2-acetoxybenzoic acid, fumaric acid, toluenesulfonic acid, methanesulfonic acid, ethane disulfonic acid, oxalic acid, or isethionic acid.

* * * * *

UNITED STATES PATENT AND TRADEMARK OFFICE
CERTIFICATE OF CORRECTION

PATENT NO. : 7,803,842 B2  
APPLICATION NO. : 11/354576  
DATED : September 28, 2010  
INVENTOR(S) : Hasmukh B. Patel It is certified that error appears in the above-identified patent and that said Letters Patent is hereby corrected as shown below:

On the Title page, item (73), in "Assignee", in column 1, line 1, delete "Hass" and insert -- Hasmukh --, therefor.

On the Title page, item (56), under "Other Publications", in column 2, line 1, delete "distributio" and insert -- distribution --, therefor.

On the Title page, item (56), under "Other Publications", in column 2, line 4, delete "Reedler," and insert -- Raedler, --, therefor.

Signed and Sealed this  
Eighteenth Day of January, 2011

David J. Kappos  
*Director of the United States Patent and Trademark Office*